(12) United States Patent
Monsonego et al.

(10) Patent No.: US 9,345,753 B2
(45) Date of Patent: May 24, 2016

(54) VACCINE FOR ALZHEIMER'S DISEASE

(75) Inventors: Alon Monsonego, Moshav Nir Banim (IL); Irun R. Cohen, Rehovot (IL)

(73) Assignees: YEDA RESEARCH AND DEVELOPMENT CO. LTD. AT THE WEIZMANN INSTITUTE OF SCIENCE, Rehovot (IL); BEN-GURION UNIVERSITY OF THE NEGEV RESEARCH AND DEVELOPMENT AUTHORITY, Beer Sheva (IL)

( * ) Notice: Subject to any disclaimer, the term of this patent is extended or adjusted under 35 U.S.C. 154(b) by 137 days.

(21) Appl. No.: 12/812,712

(22) PCT Filed: Jan. 15, 2009

(86) PCT No.: PCT/IL2009/000066
§ 371 (c)(1),
(2), (4) Date: Nov. 12, 2010

(87) PCT Pub. No.: WO2009/090650
PCT Pub. Date: Jul. 23, 2009

(65) Prior Publication Data
US 2011/0076323 A1 Mar. 31, 2011

Related U.S. Application Data

(60) Provisional application No. 61/021,348, filed on Jan. 16, 2008.

(51) Int. Cl.
*A61K 39/385* (2006.01)
*A61K 39/00* (2006.01)

(52) U.S. Cl.
CPC ......... *A61K 39/0005* (2013.01); *A61K 39/0007* (2013.01); *A61K 2039/55555* (2013.01); *A61K 2039/6043* (2013.01); *A61K 2039/64* (2013.01)

(58) Field of Classification Search
CPC ............ A61K 39/007; A61K 2039/64; A61K 2039/6043; A61K 2039/57; A61K 2039/55555; A61K 2039/645
See application file for complete search history.

(56) References Cited

U.S. PATENT DOCUMENTS

| 4,073,943 | A | 2/1978 | Wretlind |
| 4,168,308 | A | 9/1979 | Wretlind |
| 4,199,565 | A * | 4/1980 | Fullerton ..................... 424/450 |
| 4,235,871 | A | 11/1980 | Papahadjopoulos |
| 4,666,829 | A | 5/1987 | Glenner |
| 5,721,130 | A | 2/1998 | Seubert |
| 5,736,146 | A | 4/1998 | Cohen |
| 5,869,058 | A | 2/1999 | Cohen |
| 5,919,480 | A | 7/1999 | Kedar |
| 5,961,970 | A | 10/1999 | Lowell |
| 6,787,138 | B1 | 9/2004 | Schenk |
| 6,787,139 | B1 | 9/2004 | Schenk |
| 6,866,849 | B2 | 3/2005 | Schenk |
| 6,866,850 | B2 | 3/2005 | Schenk |
| 6,946,135 | B2 | 9/2005 | Schenk |
| 6,962,707 | B2 | 11/2005 | Schenk |
| 6,982,084 | B2 | 1/2006 | Schenk |
| 7,332,527 | B2 | 2/2008 | Bronich |
| 7,413,538 | B1 | 8/2008 | New |
| 2002/0037290 | A1 | 3/2002 | Armen |
| 2002/0094335 | A1 | 7/2002 | Chalifour |
| 2002/0146759 | A1 | 10/2002 | Albani |
| 2003/0171280 | A1 | 9/2003 | Soderstrom |
| 2005/0175626 | A1 | 8/2005 | Delacourte |
| 2006/0093612 | A1 * | 5/2006 | Srivastava ................... 424/185.1 |
| 2006/0121038 | A9 | 6/2006 | Schenk |
| 2009/0269370 | A1 * | 10/2009 | Cohen et al. ............. 424/197.11 |

FOREIGN PATENT DOCUMENTS

| WO | 90/10449 | 9/1990 |
| WO | WO 0152890 A1 * | 7/2001 |
| WO | WO 0234777 A1 * | 5/2002 |
| WO | 2005058940 A2 | 6/2005 |
| WO | 2006/097914 | 9/2006 |

OTHER PUBLICATIONS

Kovacs JM et al. Determination of intrinsic hydrophilicity/hydrophobicity of amino acid side chains in peptides in the absence of nearest-neighbor or conformation effects. Biopolymers, 2006; 84(3):283-297.*
Lemere CA et al. Amyloid-beta immunotherapy for the prevention and treatment of Alzheimer's disease: lessons from mice, monkeys, and humans. Rejuvenation Res. 2006; 9(1):77-84.*
Vickers JC. A vaccine against Alzheimer's disease: developments to date. Drugs Aging. 2002; 19(7):487-494.*
Amir-Kroll H et al. (2006) A conjugate vaccine composed of a heat shock protein 60 T-cell epitope peptide (p458) and Neisseria meningitidis type B capsular polysaccharide. Vaccine, 24:6555-6563.*
Adler A. et al., "Allogeneic human liposomal melanoma vaccine with or without IL-2 in metastatic melanoma patients: clinical and immunobiological effects", Cancer Biother. 10:293-306 (1995).
Agadjanyan et al., "Prototype Alzheimer's disease vaccine using the immunodominant B cell epitope from beta-amyloid and promiscuous T cell epitope pan HLA DR-binding peptide", J Immunol. 174:1580-1586 (2005).
Anderton et al., "Inflammation activates self hsp60-specific T cells", Eur J Immunol. 23:33-38 (1993).
Bard et al., "Epitope and isotype specificities of antibodies to beta-amyloid peptide for protection against Alzheimer's disease-like neuropathology", Proc Nat Acad Sci. 100:2023-2028 (2003).
Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guérin priming", Eur J Immuol. 22:1365-1372 (1992).

(Continued)

*Primary Examiner* — Kimberly A. Ballard
(74) *Attorney, Agent, or Firm* — Vorys, Sater, Seymour and Pease LLP

(57) ABSTRACT

Compositions and methods for prevention and treatment of Alzheimer's disease utilize a combination of amyloid-beta protein or a fragment thereof and a heat shock protein or a fragment thereof.

7 Claims, 11 Drawing Sheets

(56) References Cited

OTHER PUBLICATIONS

Cribbs et al., "Adjuvant-dependent modulation of Th1 and Th2 responses to immunization with beta-amyloid", Int Immunol. 15:505-514 (2003).
Cummings, "Alzheimer's disease", N Engl J Med. 351:56-67 (2004).
Dodart et al., "Immunization reverses memory deficits without reducing brain Abeta burden in Alzheimer's disease model", Nat Neurosci. 5:452-457 (2002).
Ferrer et al., "Neuropathology and pathogenesis of encephalitis following amyloid-beta immunization in Alzheimer's disease", Brain Pathol. 14:11-20 (2004).
Ghochikyan et al., "Generation and characterization of the humoral immune response to DNA immunization with a chimeric beta-amyloid-interleukin-4 minigene", Eur J Immunol. 33:3232-3241 (2003).
Gilman et al., "Clinical effects of Abeta immunization (AN1792) in patients with AD in an interrupted trial", Neurology. 64:1553-1562 (2005).
Glenner and Wong, "Alzheimer's disease: initial report of the purification and characterization of a novel cerebrovascular amyloid protein", Biochem Biophys Res Commun. 120(3):885-890 (1984).
Glenner and Wong, "Alzheimer's disease and Down's syndrome: sharing of a unique cerebrovascular amyloid fibril protein", Biochem Biophys Res Commun. 122(3):1131-1135 (1984).
Hardy, "Amyloid, the presenilins and Alzheimer's disease", Trends Neurosci. 20:154-159 (1997).
Henikoff and Henikoff, "Amino acid substitution matrices from protein blocks", Proc Natl Acad Sci USA 89:10915 (1989).
Hermann et al., "Synovial fluid-derived Yersinia-reactive T cells responding to human 65-kDa heat-shock protein and heat-stressed antigen-presenting cells", Eur J Immunol. 21:2139-2143 (1991).
Hock et al., "Antibodies against beta-amyloid slow cognitive decline in Alzheimer's disease", Neuron 38:547-554 (2003).
Jindal et al., "Primary structure of a human mitochondrial protein homologous to the bacterial and plant chaperonins and to the 65-kilodalton mycobacterial antigen", Mol Cell Biol. 9:2279-2283 (1989).
Kim et al., "Enhancing Th2 immune responses against amyloid protein by a DNA prime-adenovirus boost regimen for Alzheimer's disease", Immunol Lett. 112:30-38 (2007).
Koga et al., "T cells against a bacterial heat shock protein recognize stressed macrophages" Science. 245:1112-1115 (1989).
Konen-Waisman et al., "Self and foreign 60-kilodalton heat shock protein T cell epitope peptides serve as immunogenic carriers for a T cell-independent sugar antigen", J Immunol. 154:5977-5985 (1995).
Konen-Waisman et al., "Self heat-shock protein (hsp60) peptide serves in a conjugate vaccine against a lethal pneumococcal infection" J Infect Dis. 179:403-413 (1999).
Maier et al., "Short amyloid-beta (Abeta) immunogens reduce cerebral Abeta load and learning deficits in an Alzheimer's disease mouse model in the absence of an Abeta-specific cellular immune response", J Neurosci. 26:4717-4728 (2006).
Monsonego et al., "Immune hyporesponsiveness to amyloid beta-peptide in amyloid precursor protein transgenic mice: implications for the pathogenesis and treatment of Alzheimer's disease", Proc Nat Acad Sci. 98:10273-10278. (2001).
Monsonego et al., "Increased T cell reactivity to amyloid beta protein in older humans and patients with Alzheimer disease", J Clin Invest 112:415-422 (2003).
Monsonego et al., "Abeta-induced meningoencephalitis is IFN-gamma-dependent and is associated with T cell-dependent clearance of Abeta in a mouse model of Alzheimer's disease", Proc Nat Acad Sci. 103:5048-5053 (2006).
Morgan et al., "A beta peptide vaccination prevents memory loss in an animal model of Alzheimer's disease", Nature. 408:982-985 (2000).
Nicoll et al., "Neuropathology of human Alzheimer disease after immunization with amyloid-beta peptide: a case report", Nat Med. 9:448-452 (2003).
Nicoll et al., "Abeta species removal after abeta42 immunization", J Neuropathol Exp Neurol. 65:1040-1048 (2006).
Pearson and Lipman, "Improved tools for biological sequence comparison", Proc Natl Acad Sci USA. 85:2444 (1988).
Petrushina et al., "Alzheimer's disease peptide epitope vaccine reduces insoluble but not soluble/oligomeric Abeta species in amyloid precursor protein transgenic mice", J Neurosci. 27:12721-12731 (2007).
Qu et al., "Gene vaccination to bias the immune response to amyloid-beta peptide as therapy for Alzheimer disease", Arch Neurol. 61:1859-1864 (2004).
Schenk et al., "Immunization with amyloid-beta attenuates Alzheimer-disease-like pathology in the PDAPP mouse", Nature. 400:173-177 (1999).
Schneider et al., "Psychosis of Alzheimer disease: validity of the construct and response to risperidone", Am J Geriatr Psychiatry. 11:414-425 (2003).
Takeda et al., "A systematic review of the clinical effectiveness of donepezil, rivastigmine and galantamine on cognition, quality of life and adverse events in Alzheimer's disease", Int J Geriatr Psychiatry. 21:17-28 (2006).
Supplementary European Search Report of counterpart European Patent Application No. 09701794.1, dated Dec. 17, 2012.
Mor and Monsonego (2006) Immunization therapy in Alzheimer's disease. Expert Rev Neurother 6(5): 653-9.
Rouvio et al., (2005) Self HSP60 peptide serves as an immunogenic carrier for a CTL epitope against persistence of murine cytomegalovirus in the salivary gland. Vaccine 23(27): 3508-3518.

* cited by examiner

VACCINE FOR ALZHEIMER'S DISEASE

RELATED APPLICATION DATA

This application is the U.S. national stage of PCT/IL2009/000066, filed Jan. 15, 2009, which claims the benefit of U.S. Provisional Application No. 61/021,348, filed Jan. 16, 2008, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 19,518 byte ASCII (text) file named "Seq_List" created on Jul. 13, 2010.

FIELD OF THE INVENTION

The present invention relates to compositions and methods for prevention and treatment of Alzheimer's disease. In particular, the invention utilizes a combination of amyloid-β protein or a fragment thereof and a heat shock protein or a fragment thereof.

BACKGROUND OF THE INVENTION

Alzheimer's disease (AD) is the most common human neurodegenerative disease, leading to cognitive and functional decline and eventual death. In the year 2000, there were 4.5 million AD patients in the United States, accounting for an annual health expenditure of over $83 billion (Cummings, 2004). As life expectancy increases in Western societies, the burden of caring for AD patients is increasing, making management of the disease a leading health priority. Current therapy for AD is mainly directed at improving symptoms, with no possibility of preventing or curing the disease. Available medications include cholinesterase inhibitors to decrease the rate of cognitive decline (Takeda et al, 2006), and psychopharmacological agents to treat psychiatric aspects (Schneider et al, 2003).

Current research is aimed at targeting neuropathological features of AD, in particular, intracellular neurofibrillar tau tangles and extracellular amyloid-β (Aβ) plaques which accumulate in brain tissue of diseased patients. The Aβ peptide, which is cleaved from the amyloid precursor protein (APP), is believed to have an important role in the onset and progression of AD.

Immunization against Aβ has emerged as a promising therapeutic approach for clearing Aβ plaques and reversing cognitive decline. Active immunization using Aβ peptide in various mouse models demonstrated the prevention of AD-like pathology in young animals and attenuation of the disease in older animals (Schenk et al, 1999); prevention of memory loss (Morgan et al, 2000), and reversal of memory deficits (Dodart et al, 2002).

The first clinical trials of immunization in human AD patients involved a vaccine (AN-1792) containing an Aβ1-42 synthetic peptide and the saponin adjuvant QS21. The trial was halted at the Phase II stage due to the development of a transient aseptic meningoencephalitis i.e. an inflammatory response, in ~6% of the patients (Gilman et al, 2005). The finding of T cell infiltration in brain tissue of affected patients suggested a T cell-mediated autoimmune response (Ferrer et al, 2004).

Despite the cessation of the trial, assessment of a cohort of the participants (30 patients) indicated that 67% of those patients generated antibodies against Aβ, and also showed significantly slower rates of decline of cognitive functions and activities of daily living, as compared to patients without such antibodies. Similar beneficial clinical effects were also present in two of the three patients who had developed immunization-related aseptic meningoencephalitis (Hock et al, 2003). Furthermore, postmortem neuropathological examination of brain tissue of immunized patients showed extensive Aβ plaque clearance in neocortex regions, although tau pathology remained, and T cell meningoencephalitis was evident in at least one patient (Nicoll et al, 2006; Nicoll et al, 2003).

Accordingly, current approaches to optimizing AD immunization are directed to eliminating the detrimental T cell response. Shorter Aβ peptides, containing up to about 15 residues of the N-terminal region have been disclosed to be useful for an AD vaccine, since that region contains the dominant B cell epitopes and substantially lacks T cell epitopes, in both mouse and human (Monsonego et al, 2001; Cribbs et al, 2003). In a mouse model system, Aβ1-11 (i.e. containing the N-terminal 11 amino acids) was found to induce antisera which bound Aβ plaques and triggered plaque clearance (Bard et al, 2003). Furthermore, murine studies showed that the MHC background strongly determines the T cell response to Aβ immunization, and that Aβ-induced encephalitis is mediated by Aβ specific T helper (Th) 1 cells (Monsonego et al, 2006). In middle aged and elderly healthy humans and in AD patients, Aβ-reactive T cell responses are directed against Aβ epitopes located in residues 16-33 (Monsonego et al, 2003).

Various adjuvants or adjuvant sequences have been combined or linked with Aβ peptides, on the basis that the adjuvant stimulates beneficial T helper (Th2) cells required for antibody production. Aβ1-15 covalently coupled to bovine serum albumin induced high titers of anti-Aβ antibodies in immunized APP transgenic mice, while immunization with Aβ1-15 alone was substantially ineffective (Monsonego et al, 2001). Similarly, a prototype AD vaccine containing Aβ1-15 in tandem with the synthetic universal Th cell pan HLA DR epitope (PADRE) produced high titers of anti-Aβ antibodies in immunized mice (Agadjanyan et al, 2005). Use of a second generation vaccine composed of two copies of Aβ1-11 fused to PADRE demonstrated a positive correlation between the concentration of induced antibody and a reduction of cerebral Aβ plaques in immunized transgenic mice with pre-existing AD-like pathology (Petrushina et al, 2007).

Another disclosure of potential AD vaccines relates to four alternative immunogens encompassing either a tandem repeat of two lysine-linked Aβ1-15 sequences (2xAβ1-15) or the Aβ1-15 sequence synthesized to a cross-species T helper cell epitope (T1-Aβ1-15) and each with the addition of a three amino acid Arg-Gly-Asp motif (R-2xAβ1-15; T1-R-Aβ1-15). Intranasal immunization of wild type mice with R-2xAβ1-15 or 2xAβ1-15 plus mutant *E. coli* heat-labile enterotoxin LT(R192G) adjuvant produced high anti-Aβ antibody titers, and in a murine AD model these vaccines significantly reduced Aβ plaque load. Administration of either T1-Aβ1-15 or T1-R-Aβ1-15 with adjuvant resulted in significantly lower anti-Aβ antibody titers (Maier et al, 2006).

Immunogenic compositions comprising a conjugate composed of a fragment of Aβ linked to a carrier molecule such as diphtheria toxoid, and an adjuvant, are disclosed for example in U.S. Pat. Nos. 6,787,138; 6,946,135 and 6,982,084. Methods of treating a disease characterized by an amyloid deposit of Aβ using such compositions are disclosed for example in U.S. Pat. Nos. 6,866,849; 6,866,850 and 6,787,139.

DNA vaccines against AD have also been described, for example a chimeric DNA minigene encoding Aβ1-42 fused to mouse IL-4 (Ghochikyan et al, 2003); a mouse Aβ1-42 dimer gene for delivery by gene gun, and plasmids encoding Aβ1-42 and Aβ1-16 (Qu et al, 2004); and an adenovirus vector AdPED1-(Aβ1-6)$_{11}$ encoding 11 tandem repeats of Aβ1-6 (Kim et al, 2007).

HSP60 belongs to a family of chaperone molecules highly conserved throughout evolution, and apparently, no cell can exist without the ability to express HSP60. The human HSP60 molecule was formerly designated HSP65, but was renamed in view of more accurate molecular weight information; as used herein both designations refer to the same protein. Mammalian HSP60 is highly homologous to the bacterial cognates, showing about 50% amino acid identity (Jindal et al, 1989). Thus, HSP60 is shared by the host and its parasites, and is immunogenic, cross-reactive, and universally expressed in inflammation. Furthermore, HSP60 is well recognized by the immune system (Konen-Waisman et al, 1999; Konen-Waisman et al, 1995) and is a part of the set of self-molecules for which autoimmunity naturally exists. Heat shock, IFNγ, bacterial or viral infection, and inflammation, all result in the presentation of endogenous HSP60 epitopes on MHC class II molecules leading to the activation of HSP60-specific T cells, even in healthy individuals (Anderton et al, 1993; Hermann et al, 1991; Koga et al, 1989).

PCT Patent Application No. WO 90/10449, of some of the present inventors, describes a peptide designated p277 having an amino acid sequence corresponding to positions 437-460 of the human HSP65 molecule that is useful as an immunogen inducing resistance to insulin dependent diabetes mellitus (IDDM). A control peptide, designated p278, corresponding to positions 458-474 of human HSP65, did not induce resistance to IDDM.

U.S. Pat. No. 5,736,146, of some of the present inventors, discloses conjugates of poorly immunogenic antigens with a synthetic peptide carrier comprising a T cell epitope derived from the sequence of human heat shock protein HSP65, or an analog thereof, said peptide or analog being capable of increasing substantially the immunogenicity of the poorly immunogenic antigen. According to the disclosure, a peptide corresponding to positions 458-474 and 437-453 of human or mouse HSP60, and homologs thereof, may be conjugated with a wide variety of antigens including peptides, proteins and polysaccharides such as bacterial polysaccharide (e.g. capsular polysaccharide (CPS) Vi of *Salmonella typhi*), and antigens derived from HIV virus or from malaria antigen.

U.S. Pat. No. 5,869,058, of some of the present inventors, discloses conjugates of poorly immunogenic antigens, e.g., peptides, proteins and polysaccharides, with a synthetic peptide carrier comprising a T cell epitope derived from the sequence of *E. coli* HSP65 (GroEL), or an analog thereof, said peptide or analog being capable of increasing substantially the immunogenicity of the poorly immunogenic antigen. According to the disclosure, a suitable peptide is Pep278e, which corresponds to positions 437-453 of the *E. coli* HSP65 molecule.

Barrios et al (1992) disclose that conjugates of 70 kDa HSP or 65 kDa with peptides or oligosaccharides produced high titers of IgG antibodies in immunized mice in the absence of any previous priming with BCG. According to the disclosure, the adjuvant-free carrier effect was T cell dependent, and the use of HSPs as carriers in conjugated constructs was suggested for human vaccine design.

PCT Patent Application No. WO 2006/097914, of some of the present inventors, discloses vaccines comprising an isolated viral antigenic peptide and a synthetic peptide derived from a T cell epitope of HSP60. According to the disclosure, the vaccines include mixtures where the peptide serves as an adjuvant, as well as conjugates where the peptide is covalently linked to the viral antigen. Disclosed peptides include p458, corresponding to positions 458-474 of mouse HSP60, and Ec27, corresponding to positions 391-410 of *E. coli* HSP60 (GroEL).

There remains an unmet need for a safe and effective vaccine which can prevent and/or attenuate the neuropathology and cognitive decline of Alzheimer's disease. The prior art does not teach or suggest a vaccine comprising an Aβ peptide in combination with a synthetic peptide based on an epitope of HSP60.

SUMMARY OF THE INVENTION

The present invention provides a vaccine composition for the treatment and prevention of Alzheimer's disease, which incorporates a fragment of Aβ comprising a B cell epitope and substantially lacking T cell epitopes, and an HSP60 peptide. An exemplary fragment of Aβ is Aβ1-15, corresponding to the first 15 amino acids derived from Aβ, and an exemplary HSP60 peptide is p458.

It is herein disclosed for the first time, that a vaccine according to the invention is effective in inducing high titers of anti-Aβ antibodies, and in clearing Aβ plaques in the brain, without the requirement of any additional adjuvant, and without the need for providing the Aβ fragment and the HSP60 peptide as a single peptide conjugate.

The principles of the invention are exemplified by experiments performed in transgenic (Tg) murine models of Alzheimer's disease. Such mice overexpress mutated forms of human amyloid precursor protein (APP), show accumulation of Aβ plaques in the brain and exhibit decreased cognitive function with age. Use of such models has resulted in the unexpected discovery that an immunizing vaccine comprising a covalent conjugate of the peptides Aβ1-15 and p4.58 induces high titers of anti-Aβ antibodies, and results in significant clearance of Aβ plaques in the brain.

Without wishing to be bound by any particular theory or mechanism of action, the vaccine of the invention may activate the Toll-like receptor (TLR) pathway so as to evoke B cell activation and specific anti-Aβ antibody production in a substantially T cell-independent fashion, and wherein the HSP60 peptide may act as an adjuvant for antibody production. The ability of the induced antibodies to clear Aβ plaques from AD diseased brain may be attributed to Fcγ-mediated uptake and clearance of Aβ-antibody complexes by local activated microglia and/or net movement of Aβ peptide out of the brain as a result of its binding and mobilization by Aβ antibodies. Furthermore, the vaccine induces only minimal T cell activation, and the induced T cell response is of the Th2 type i.e an anti-inflammatory response, in contrast to a Th1 type response which is associated with pro-inflammatory responses.

Moreover, the vaccine of the present invention is advantageous over prior art vaccines against AD, since it is capable of inducing an antibody response in the absence of a conventional adjuvant, and its use is not associated with harmful T cell responses. In addition, the efficacy of the subject vaccine may not be dependent on the Major Histocompatability Complex (MHC; also known as Human Leukocyte Antigen (HLA) in humans) genetic background of the vaccinated subject, since the TLR pathway is MHC-independent, in contrast to the T cell dependent pathway on which prior art vaccines are based. Furthermore, effective immunization may be achieved with the subject vaccine when the Aβ fragment and the HSP60 peptide are injected as a mixture, in contrast to many prior art vaccines which require an Aβ fragment conjugated to an immunostimulatory peptide sequence.

In a first aspect, there is provided a vaccine composition for the prevention and/or treatment of a neurological disorder associated with Aβ plaque accumulation, the vaccine composition comprising an isolated Aβ peptide and an isolated HSP60 peptide (the latter is also referred to herein as an "HSP60 epitope"). In a particular embodiment, the vaccine comprises an admixture of the Aβ peptide and the HSP60 peptide. In a particular embodiment, the vaccine comprises a covalent conjugate of the Aβ peptide and the HSP60 peptide. In a particular embodiment, the vaccine comprises a synthetic peptide carrier. In a particular embodiment, the synthetic peptide carrier is multimeric. In a particular embodiment, the multimeric synthetic peptide carrier comprises a plurality of HSP60 peptide units. In a particular embodiment, the vaccine comprises a multimeric carrier comprising a plurality of HSP60 peptide units, wherein each HSP60 peptide unit is conjugated directly to an Aβ peptide. In another embodiment, each HSP60 peptide unit is conjugated to an Aβ peptide indirectly via conjugation to other peptide units. In a particular embodiment of the vaccine, the molar ratio of the HSP60 peptide to the Aβ peptide is in excess of 1:1. In a particular embodiment, the molar ratio of the HSP60 peptide to the Aβ peptide in the multimeric synthetic peptide carrier is in excess of 1:1.

In particular embodiments, the Aβ peptide is selected from the group consisting of Aβ1-42 (SEQ ID NO: 7); Aβ1-40 (SEQ ID NO: 8); Aβ1-15 (SEQ ID NO: 9); Aβ1-11 (SEQ ID NO: 10) and Aβ1-12 (SEQ ID NO: 11). In a particular embodiment, the Aβ peptide is Aβ1-15 (SEQ ID NO: 9).

In a particular embodiment, the HSP60 peptide is suitable to enhance the immunogenicity of the Aβ peptide without producing adverse side effects due to undesirable T cell responses. Enhanced immunogenicity of the Aβ peptide may be measured by serum titer of antibodies directed to Aβ1-42.

According to some embodiments, the HSP60 peptide and/or the synthetic peptide carrier comprise the known peptide p458, an MHC class II-restricted peptide derived from murine HSP60 (corresponding to amino acids 458-474 of murine HSP60; this peptide also designated previously as p278m), or an analog or derivative thereof. In other embodiments, the HSP60 peptide and/or the synthetic peptide carrier comprises the known peptide carrier Ec27, a peptide derived from *E. coli* HSP60 (corresponding to amino acids 391-410 of *E. coli* HSP60). *E. coli* HSP60, also known as GroEL, corresponds to accession number gi: 536987 (SEQ ID NO: 14).

It is to be explicitly understood that recitation of a particular peptide from a particular species also encompasses the corresponding peptide from a different species. Thus for example, p458 includes both murine p458 and human 458. Analogs, fragments, derivatives, conjugates and salts of the recited peptides are also contemplated by the invention.

In a particular embodiment, the HSP60 peptide is selected from the group consisting of:
  (a) NEDQKIGIEIIKRTLKI (p458h; SEQ ID NO: 1);
  (b) NEDQKIGIEIIKRALKI (p458; SEQ ID NO:2);
  (c) EGDEATGANIVKVALEA (p458mt; SEQ ID NO:3);
  (d) NEDQNVGIKVALRAMEA (p458e; SEQ ID NO:4);
  (e) KKARVEDALHATRAAVEEGV (Ec27; SEQ ID NO:5);
  (f) KKDRVTDALNATRAAVEEGI (Ec27h; SEQ ID NO:6), and
  (g) an analog of p458h (SEQ ID NO: 1) wherein the analog has at least 70% of the electric and hydrophilicity/hydrophobicity characteristic of human HSP60 from position 458 to position 474.

In one embodiment, the HSP60 peptide is an analog of p458h (SEQ ID NO: 1): $^{458}$NEDQKIGIEIIKRTLKI$^{474}$ in which the residue $E^{459}$ is either E or D; the residue $D^{460}$ is either D or E; the residue $K^{462}$ is either K or R or ornithine (Orn); the residue $I^{463}$ is either I or L, V, M, F, norleucine (Nle) or norvaline (Nva); the residue $I^{465}$ residue is either I or L, V, M, F, Nle or Nva; the residue $E^{466}$ is either E or D; the residue $I^{467}$ is either I or L, V, M, F, Nle or Nva; the residue $I^{468}$ is either I or L, V, M, F, Nle or Nva; the residue $K^{469}$ is either K or R or Orn; the residue $R^{470}$ is either R, K or Orn; the residue $L^{472}$ in either L or I, V, M, F, Nle or Nva; the residue $K^{473}$ is either K or R or Orn; and the residue $I^{474}$ is either I or L, V, M, F, Nle or Nva.

In other embodiments, the HSP60 peptide may correspond to a complete HSP60 protein sequence, such as that of *E. coli* GroEL (gi: 536987; SEQ ID NO: 14); human HSP60 (gi: 49522865; SEQ ID NO: 15), or mouse HSP60 (gi: 31981679; SEQ ID NO: 16).

In a particular embodiment, the vaccine composition comprises the peptide Aβ1-15 (SEQ ID NO: 9) and the peptide p458h (SEQ ID NO: 1). In a particular embodiment, the vaccine composition comprises an admixture of Aβ1-15 (SEQ ID NO: 9) and p458h (SEQ ID NO: 1).

In a particular embodiment, the vaccine composition comprises a covalent conjugate of Aβ1-15 and p458, wherein the covalent conjugate comprises SEQ ID NO: 13. As used herein, the designation Aβ1-15-p458 refers to SEQ ID NO: 13. In a particular embodiment, the vaccine comprises a covalent conjugate of Aβ1-42 and p458, wherein the covalent conjugate comprises SEQ ID NO: 12. In a particular embodiment, the vaccine composition comprises a covalent conjugate of Aβ1-15 and p458h, wherein the covalent conjugate comprises SEQ ID NO: 17. In particular embodiments, the covalent conjugate is a product of chemical synthesis.

In a particular embodiment, the vaccine composition further comprises at least one pharmaceutically acceptable carrier, excipient or diluent. In a particular embodiment, the carrier is selected from the group consisting of liposomes and micelles. In a particular embodiment, the vaccine composition is substantially free of adjuvant. Alternately and optionally, the vaccine composition may further comprise an adjuvant. When an adjuvant is included in the vaccine composition, it is preferably one which is not associated with Th-17 responses, such as an aluminum-based adjuvant.

In a particular embodiment, the vaccine composition comprises liposomes, wherein the liposomes comprise the Aβ peptide and the HSP60 peptide. In a particular embodiment, the Aβ peptide and the HSP60 peptide are co-encapsulated within the same liposomes. In a particular embodiment, a covalent conjugate of the Aβ peptide and the HSP60 peptide is encapsulated in liposomes. In a particular embodiment, the Aβ peptide and the HSP60 peptide are encapsulated within different liposomes. In a particular embodiment, the Aβ peptide and the HSP60 peptide are displayed on the outer surface of the liposome. In a particular embodiment, a covalent conjugate of the Aβ peptide and the HSP60 peptide is displayed on the outer surface of liposomes. In a particular embodiment, the liposomes comprise a covalent conjugate comprising a sequence selected from SEQ ID NO: 13 and SEQ ID NO: 17. In a particular embodiment, the liposomes comprise an Aβ peptide encapsulated therein and an HSP60 peptide displayed on the outer surface of the liposome. In a particular embodiment, the liposomes comprise an HSP60 peptide encapsulated therein and an Aβ peptide displayed on the outer surface of the liposome. In particular embodiments, the liposomes comprise a complete HSP60 protein sequence, such as that of *E. coli* GroEL (SEQ ID NO: 14); human HSP60 (SEQ ID NO: 15), or mouse HSP60 (SEQ ID NO: 16).

In a particular embodiment, there is provided a method for preparing the vaccine composition of the invention, wherein the method comprises providing the Aβ peptide and the HSP60 peptide as an admixture, together with at least one pharmaceutically acceptable carrier, excipient or diluent. In a particular embodiment, the method comprises preparing a covalent conjugate of the Aβ peptide and the HSP60 peptide, and combining the conjugate with a pharmaceutically acceptable carrier, excipient or diluent. In a particular embodiment, the carrier is selected from the group consisting of liposomes and micelles. In a particular embodiment, the vaccine composition is substantially free of adjuvant. Alternately and optionally, the vaccine composition may further comprise an adjuvant.

According to a second aspect, there is provided a method for preventing or treating a neurological disorder associated with Aβ plaque accumulation, the method comprising the step of: administering to a subject in need thereof with a therapeutically effective amount of a therapeutic composition, wherein the composition comprises an isolated Aβ peptide and an isolated HSP60 peptide; thereby preventing or treating the neurological disorder. In a particular embodiment, the composition comprises an admixture of the Aβ peptide and the HSP60 peptide. In a particular embodiment, the composition comprises a covalent conjugate of the Aβ peptide and the HSP60 peptide. In particular embodiments, the Aβ peptide is selected from the group consisting of Aβ1-42 (SEQ ID NO: 7); Aβ1-40 (SEQ ID NO: 8); Aβ1-15 (SEQ ID NO: 9) and Aβ1-11 (SEQ ID NO: 10). In a particular embodiment, the Aβ peptide is Aβ1-15 (SEQ ID NO: 9).

In a particular embodiment, the HSP60 peptide is selected from the group consisting of:
(a) NEDQKIGIEIIKRTLKI (p458h; SEQ ID NO: 1);
(b) NEDQKIGIEIIKRALKI (p458; SEQ ID NO:2);
(c) EGDEATGANIVKVALEA (p458mt; SEQ ID NO:3);
(d) NEDQNVGIKVALRAMEA (p458e; SEQ ID NO:4);
(e) KKARVEDALHATRAAVEEGV (Ec27; SEQ ID NO:5);
(f) KKDRVTDALNATRAAVEEGI (Ec27h; SEQ ID NO:6), and
(g) an analog of p458h (SEQ ID NO: 1) wherein the analog has at least 70% of the electric and hydrophilicity/hydrophobicity characteristic of human HSP60 from position 458 to position 474.

In one embodiment, the HSP60 peptide is an analog of p458h (SEQ ID NO: 1): $^{458}$NEDQKIGIEIIKRTLKI$^{474}$ in which the residue $E^{459}$ is either E or D; the residue $D^{460}$ is either D or E; the residue $K^{462}$ is either K or R or ornithine (Orn); the residue $I^{463}$ is either I or L, V, M, F, norleucine (Nle) or norvaline (Nva); the residue $I^{465}$ residue is either I or L, V, M, F, Nle or Nva; the residue $E^{466}$ is either E or D; the residue $I^{467}$ is either I or L, V, M, F, Nle or Nva; the residue $I^{468}$ is either I or L, V, M, F, Nle or Nva; the residue $K^{469}$ is either K or R or Orn; the residue $R^{470}$ is either R, K or Orn; the residue $L^{472}$ in either L or I, V, M, F, Nle or Nva; the residue $K^{473}$ is either K or R or Orn; and the residue $I^{474}$ is either I or L, V, M, F, Nle or Nva.

In other embodiments, the HSP60 peptide may correspond to a complete HSP60 protein sequence, such as that of *E. coli* GroEL (gi: 536987; SEQ ID NO: 14); human HSP60 (gi: 49522865; SEQ ID NO: 15), or mouse HSP60 (gi: 31981679; SEQ ID NO: 16).

In a particular embodiment, the vaccine composition comprises the peptide Aβ1-15 (SEQ ID NO: 9) and the peptide p458h (SEQ ID NO: 1). In a particular embodiment, the vaccine composition comprises an admixture of Aβ1-15 (SEQ ID NO: 9) and p458h (SEQ ID NO: 1). In a particular embodiment, the composition comprises a covalent conjugate of Aβ1-15 and p458, wherein the covalent conjugate comprises SEQ ID NO:13. In a particular embodiment, the vaccine composition comprises a covalent conjugate of Aβ1-42 and p458, wherein the covalent conjugate comprises SEQ ID NO:12. In a particular embodiment, the vaccine composition comprises a covalent conjugate of Aβ1-15 and p458h, wherein the covalent conjugate comprises SEQ ID NO: 17). In a particular embodiment, the composition further comprises a pharmaceutically acceptable carrier, excipient or diluent. In a particular embodiment, the carrier is selected from the group consisting of liposomes and micelles. In a particular embodiment, the composition is substantially free of adjuvant. Alternately and optionally, the composition may further comprise an adjuvant. When an adjuvant is included in the composition, it is preferably one which is not associated with Th-17 responses, such as an aluminum-based adjuvant. In a particular embodiment, the composition comprises liposomes, wherein the liposomes comprise the Aβ peptide and the HSP60 peptide. In a particular embodiment, the Aβ peptide and the HSP60 peptide are co-encapsulated within the same liposomes. In a particular embodiment, a covalent conjugate of the Aβ peptide and the HSP60 peptide is encapsulated in liposomes. In a particular embodiment, the Aβ peptide and the HSP60 peptide are separately encapsulated within different liposomes. In a particular embodiment, the Aβ peptide and the HSP60 peptide are displayed on the outer surface of the liposome. In a particular embodiment, a covalent conjugate of the Aβ peptide and the HSP60 peptide is displayed on the outer surface of liposomes. In a particular embodiment, the liposomes comprise a covalent conjugate comprising a sequence selected from SEQ ID NO: 13 and SEQ ID NO: 17. In a particular embodiment, the liposomes comprise an Aβ peptide encapsulated therein and an HSP60 peptide displayed on the outer surface of the liposome. In a particular embodiment, the liposomes comprise an HSP60 peptide encapsulated therein and an Aβ peptide displayed on the outer surface of the liposome. In particular embodiments, the liposomes comprise a complete HSP60 protein sequence, such as that of *E. coli* GroEL (SEQ ID NO: 14); human HSP60 (SEQ ID NO: 15), or mouse HSP60 (SEQ ID NO: 16).

In a particular embodiment, the neurological disorder is selected from the group consisting of Alzheimer's disease and Down's syndrome. In a particular embodiment, the neurological disorder is Alzheimer's disease. In a particular embodiment, the neurological disorder is associated with a mutation in a gene encoding a protein selected from the group consisting of amyloid precursor protein (APP) and presenilin.

In a particular embodiment, the administering comprises administering the composition at regular intervals over a period of one month to two years. In a particular embodiment, the regular intervals are from once a week to once every four weeks. In a particular embodiment, the composition is administered at a concentration of 0.1 to 3 mg/ml. In a particular embodiment, the composition is administered at a concentration of 1 mg/ml.

In a particular embodiment, the method further comprises assaying the level of anti-Aβ1-42 antibodies in the serum of the subject prior to and following the administering step. In a particular embodiment, the assaying comprises the use of an ELISA technique.

In a particular embodiment, the method further comprises assessing the level of cognitive function in the subject prior to and following the administering step, wherein an improvement in the level of cognitive function is indicative of the efficacy of the method.

In a particular embodiment, the administering is carried out by a route selected from the group consisting of intramuscular; intravenous; intradermal; transcutaneous; intranasal, oral, intraperitoneal and subcutaneous.

In a particular embodiment, the subject is a human or a non-human mammal.

In another aspect of the invention, there is provided a use of an isolated Aβ peptide and an isolated HSP60 peptide for the preparation of a vaccine composition for the prevention and/or treatment of a neurological disorder associated with Aβ plaque accumulation.

In another aspect of the invention, there is provided a therapeutic composition for preventing and/or treating a neurological disorder associated with Aβ plaque accumulation, the vaccine composition comprising an admixture of an isolated Aβ peptide and an isolated ligand for a Toll-like receptor. In a particular embodiment, the ligand for the Toll-like receptor comprises an HSP60 peptide. In a particular embodiment, the ligand for the Toll-like receptor comprises a complete HSP60 protein sequence.

In another aspect of the invention, there is provided a vaccine composition for preventing and/or treating a neurological disorder associated with Aβ plaque accumulation, the vaccine composition comprising an admixture of an isolated Aβ peptide and an isolated ligand for a T cell receptor. In a particular embodiment, the ligand for the T cell receptor comprises an HSP60 peptide. In a particular embodiment, the ligand for the T cell receptor comprises a complete HSP60 protein sequence.

Other objects, features and advantages of the present invention will become clear from the following description and drawings.

BRIEF DESCRIPTION OF THE FIGURES

FIG. 9 illustrates spleen T cell responses in humanized HLA DR15/APP Tg mice following vaccination with the indicated doses of Aβ1-15-p458 or Aβ1-42.

DETAILED DESCRIPTION OF THE INVENTION

Figure 1:
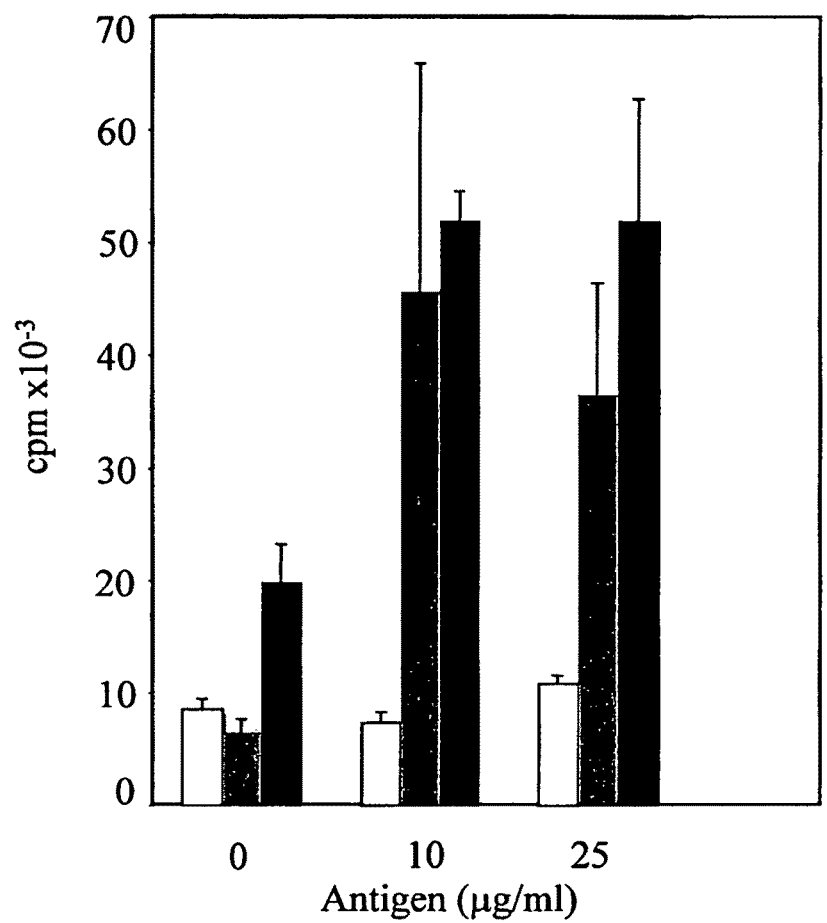
FIG. 1 illustrates ex-vivo proliferation of HSP-specific T cells in SJL mice (black bars) and humanized HLA DRB1-1501 Tg mice (gray bars). Following vaccination with p458, antigen-specific T-cell proliferation was induced in SJL mice and HLA DRB1-1501 Tg mice, but not in C57BL6 mice (white bars).

The present invention provides novel vaccines which are effective for the prevention and treatment of neurological disorders characterized by the accumulation of Aβ plaques in the brain, such as Alzheimer's disease. The vaccine of the invention comprises an Aβ peptide and an HSP60 peptide. A particularly suitable Aβ peptide is that corresponding to amino acid residues 1 to 15 (Aβ1-15) of Aβ1-42, since this N-terminal region contains B cell epitopes required for specific antibody induction, yet substantially lacks T cell epitopes, the latter of which have been associated with undesirable immunological responses in vaccinated subjects. A particularly suitable HSP60 epitope is the synthetic peptide designated p458, which is an MHC class II-restricted peptide derived from murine HSP60 (corresponding to amino acids 458-474 of murine HSP60, this peptide also designated previously as p278m). It is now disclosed for the first time that p458 substantially increases the immunogenicity of Aβ1-15 when the peptides are present together either as an admixture or in a covalent conjugate, and furthermore results in an immune response which is primarily of the Th2 type.

By "immunogenicity" it is specifically intended to mean the induction of a specific B cell response resulting in the production of antibodies which specifically interact with a desired antigen, such as Aβ1-42, as well as the presentation of such antibodies. The invention also encompasses vaccines comprising homologs, analogs and derivatives of p458, inasmuch as they are capable of augmenting the immunogenicity of Aβ peptide in a vaccinated subject. The invention further provides novel mixtures, conjugates and methods of preparation and use of the vaccine compositions of the invention.

The present invention is based in part, on studies of the effects of a chimeric peptide, corresponding to a covalent conjugate of Aβ1-15 and p458 (herein designated Aβ1-15-p458), when administered to transgenic mouse models of Alzheimer's disease. As described in Example 2, vaccination and boosting of mice with Aβ1-15-p458 emulsified in an adjuvant resulted in higher serum titers of antibodies specific for Aβ1-42, as compared to mice vaccinated with Aβ1-42 emulsified in the same adjuvant. As described in Examples 3 and 5, repeated vaccination of mice with Aβ1-15-p458 resulted in increasing production of antibodies specific for Aβ1-42. The IgG antibodies produced were primarily of the IgG1 and IgG2b isotypes, indicative of a Th2 type immune response. As described in Examples 4 and 5, brains of mice vaccinated with Aβ1-15-p458 showed decreased staining of Aβ plaques and reduced microglial activation as compared to control mice, indicative of vaccine-induced clearance of neuropathological plaques. As described in Example 6, T cell responses in mice vaccinated with Aβ1-15-p458 were significantly lower than that of mice vaccinated with Aβ1-42. In particular, the former group produced significantly less Th1 cytokine and growth factor, as compared to the latter group.

DEFINITIONS

As used herein, the singular forms "a", "an" and "the" include plural forms unless the context clearly dictates otherwise. Thus, for example, reference to "an Aβ peptide" includes combinations of Aβ peptides, and so forth.

As used herein, the terms "vaccine", "vaccine composition" and "therapeutic composition" interchangeably refer to a composition comprising a particular antigen, which upon administration to a subject, induces a specific beneficial immune response against that antigen and against related antigens sharing the same or similar epitopes. The beneficial immune response results in a substantial reduction of the severity or progression of a particular disease in the subject, or in the substantial prevention of signs and symptoms of a particular disease in the subject. In the context of the present invention, the vaccine is intended for the treatment and prevention of diseases characterized by Aβ plaque accumulation in brain tissue, such as AD. Accordingly, related terms such as "vaccination" and "vaccinate" refer to administration of the vaccine or therapeutic composition.

As used herein "epitope" or "antigenic determinant" refers to a site on an antigen to which B and/or T cells respond. B cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope, by antigen-dependent killing (cytotoxic T lymphocyte assay) or by cytokine secretion, as is known in the art.

As used herein "therapeutically effective amount" refers to an amount of the composition of the invention, which upon administration to a subject in one or more doses, results in a substantial reduction of the severity or progression of a disease characterized by Aβ plaque accumulation, or in the substantial prevention of signs and symptoms of a disease characterized by Aβ plaque accumulation.

As used herein "covalent conjugate" refers to a chimeric peptide comprising an Aβ peptide and an HSP60 epitope, linked either as a continuous fusion peptide or by means of chemical conjugation (either directly or through a spacer), using methods well known in the art.

As used herein "admixture" refers to a combination of two or more peptides without any direct covalent linkage between them. An admixture however, may be present in a carrier system such as a liposomal preparation.

As used herein, an "immune" or "immunological" response refers to the development of a humoral (antibody mediated) and/or a cellular (mediated by antigen-specific T cells or their secretion products) response directed against an Aβ peptide in a recipient subject. A humoral response may be T cell dependent, involving activation of T cells and secretion of cytokines with Th1 (proinflammatory) or Th2 (anti-inflammatory) phenotypes. Alternately or in addition, a humoral response may be T cell independent. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating IgG and T cells from an immunized syngeneic animal and measuring protective or therapeutic effect in a second subject.

Compositions of the Invention

The vaccine composition of the invention comprises an isolated Aβ peptide and an isolated peptide comprising an epitope of HSP60. These distinct peptides may be joined together in a covalent conjugate, or alternately may be found together in an admixture.

In some aspects of the invention, the vaccine composition may comprise an admixture of an isolated Aβ peptide and an isolated ligand for a Toll-like receptor, or an admixture of an isolated Aβ peptide and an isolated ligand for a T cell receptor. In particular embodiments, the ligand for the Toll-like receptor is an HSP60 peptide. In a particular embodiment, the ligand for the Toll-like receptor comprises a complete HSP60 protein sequence. In particular embodiments, the ligand for the T cell receptor is an HSP60 peptide. In a particular embodiment, the ligand for the T cell receptor comprises a complete HSP60 protein sequence.

β-amyloid peptide, also known as Aβ or A4 peptide (see U.S. Pat. No. 4,666,829; Glenner et al (1984) Biochem Biophys Res Commun 120, 1131), is a peptide of 39-43 amino acids, which is the principal component of characteristic plaques of Alzheimer's disease. Aβ is generated by processing of the larger protein amyloid precursor protein (APP) by two enzymes, termed β- and γ-secretases (Hardy (1997) Trends Neurosci 20, 154-159). Known mutations in APP associated with Alzheimer's disease occur proximate to the site of β- or γ-secretase cleavage, or within Aβ. For example, position 717 is proximate to the site of γ-secretase cleavage of APP in its processing to Aβ, and positions 670/671 are proximate to the site of β-secretase cleavage. It is believed that the mutations cause AD disease by interacting with the cleavage reactions by which Aβ is formed so as to increase the amount of the 42/43 amino acid form of Aβ generated.

Aβ has the ability to fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 fold increase in activation of these cells. This mechanism causes Aβ to generate an immune response in excess of that of other antigens.

The isolated Aβ peptide used in the present invention may be any of the naturally occurring forms of Aβ peptide or a fragment thereof. For example, human forms of Aβ include Aβ1-39, Aβ1-40, Aβ1-41, Aβ1-42 and Aβ1-43, as described for example, in Hardy, supra. The Aβ peptide is preferably one which primarily includes only B cell epitopes found within the N-terminal region, and substantially lacks T cell epitopes found in the C-terminal region. Suitable Aβ peptides for use in the present invention include, but are not limited to Aβ1-42 (SEQ ID NO:7); Aβ1-40 (SEQ ID NO:8); Aβ1-15 (SEQ ID NO:9); Aβ1-11 (SEQ ID NO:10), and Aβ1-12 (SEQ ID NO:11). A currently preferred Aβ peptide is Aβ1-15 (SEQ ID NO: 9).

The isolated Aβ peptide can be any active fragment, homolog or analog of a natural Aβ peptide that contains an epitope that induces a protective or therapeutic immune response upon administration to a subject. Suitable fragments typically have a sequence of at least 3, 5, 6, 10 or 20 contiguous amino acids from a natural peptide. Analogs of Aβ peptides include allelic, species and induced variants. Species analogs may also be termed homologs. Analogs typically differ from naturally occurring peptides at one or a few positions, often by virtue of conservative substitutions. With respect to Aβ peptides, "analogs" typically exhibit at least 80 or 90% sequence identity with natural Aβ peptides. In some embodiments, a suitable Aβ analog exhibits substantial identity with a naturally occurring Aβ peptide or fragment thereof.

In some embodiments, a suitable Aβ analog may include unnatural amino acids or modifications of N or C terminal amino acids. Examples of unnatural amino acids are α,α-disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine and ω-N-methylarginine. Fragments and analogs can be screened for prophylactic or therapeutic efficacy in transgenic animal models as described below.

The HSP60 peptide (also referred to herein as an "HSP60 epitope") used in the vaccine of the invention is one which increases, enhances or promotes the immunogenicity of the Aβ peptide. Enhanced immunogenicity of the Aβ peptide may be measured by serum titer of antibodies directed to Aβ1-42, as described below.

In particular embodiments, the HSP60 peptide forms part of a synthetic peptide carrier. Such a synthetic peptide carrier may comprise more than one copy of the HSP60 peptide, thus providing a multimeric carrier. Multiple copies of the HSP60 peptide may advantageously promote even greater immunogenicity of the Aβ peptide component of the vaccine, as compared to a vaccine comprising a single copy of the HSP60 peptide.

In some embodiments, the vaccine comprises such a multimeric synthetic peptide carrier. To form a vaccine from the multimeric carrier, each HSP60 peptide unit may be conjugated directly to an Aβ peptide, or indirectly via conjugation to other peptide units forming e.g. a dendrimer or a fusion peptide comprising multiple HSP60 peptide carrier units in tandem. For instance, a carrier may comprise two p458h peptides in tandem.

Accordingly, in particular embodiments, the molar ratio of the HSP60 peptide to the Aβ peptide is in excess of 1:1. In a particular embodiment, the molar ratio of the HSP60 peptide to the Aβ peptide in the multimeric synthetic peptide carrier is in excess of 1:1.

A vaccine composition comprising a multimeric carrier may be created, for example, by means of chemically conjugating the Aβ peptides with the HSP60 carrier peptides, directly or via a spacer, using methods well known in the art. Both homobifunctional and heterobifunctional linkers are available commercially, for example, from Pierce Chemical Company, Rockford, Ill., USA.

As can be appreciated by those of skill in the art, the actual number of HSP60 peptide units per Aβ peptide in a population of conjugates formed via conventional chemical conjugation methods varies from molecule to molecule within the population. The multimeric carriers of the invention and the conjugates and compositions comprising them may be characterized by at least 30 covalently attached units of p458 or analogs and derivatives thereof in average per molecule. In another embodiment, said conjugates have a molar ratio of HSP60 peptide to Aβ peptide that is greater than about 30:1, preferably greater than about 40:1, 50:1, 60:1, 70:1, 80:1, 90:1, 100:1, or 200:1.

Alternately or in addition, a multimeric carrier may be created using liposomes, for example when the HSP60 epitope is present in multiple copies on the outside of a liposome.

According to some embodiments, the HSP60 peptide comprises the known peptide designated p458, a Major Histocompatibility Complex (MHC) class II-restricted peptide derived from murine HSP60 (corresponding to amino acids 458-474 of murine HSP60, this peptide also designated previously as p278m), or an analog or derivative thereof. In other embodiments, the HSP60 epitope comprises the known peptide designated Ec27, a peptide derived from *E. coli* HSP60 (corresponding to amino acids 391-410 *E. coli* HSP60). *E. coli* HSP60, also known as GroEL, corresponds to accession number gi: 536987 (SEQ ID NO: 14).

It is to be explicitly understood that recitation of a particular peptide from a particular species also encompasses the corresponding peptide from a different species. Thus for example, p458 includes both murine p458 and human 458. Analogs, fragments, derivatives, conjugates and salts of the recited peptides are also contemplated by the invention.

Suitable HSP60 peptides include the following:
 (a) NEDQKIGIEIIKRTLKI (p458h; SEQ ID NO: 1);
 (b) NEDQKIGIEIIKRALKI (p458; SEQ ID NO:2);
 (c) EGDEATGANIVKVALEA (p458mt; SEQ ID NO:3);
 (d) NEDQNVGIKVALRAMEA (p458e; SEQ ID NO:4);
 (e) KKARVEDALHATRAAVEEGV (Ec27; SEQ ID NO:5);
 (f) KKDRVTDALNATRAAVEEGI (Ec27h; SEQ ID NO:6), and
 (g) an analog of p458h (SEQ ID NO: 1) wherein the analog has at least 70% of the electric and hydrophilicity/hydrophobicity characteristic of human HSP60 from position 458 to position 474.

The peptide p458 is characterized by possessing a relatively high charge, i.e. strong electric properties (7 out of 17 constituent amino acid residues of p458 are either negatively or positively charged) and high hydrophobicity (6 amino acid residues). The peptide p458h is further characterized by possessing a polar negatively-charged N-terminal domain, a polar positively-charged C-terminal domain and a highly hydrophobic core. Advantageously, these overall features should be maintained when designing analogs of HSP60 epitopes in order to preserve efficacy. Thus, following the above general outline certain amino acids substitution will lead to active peptides. More specifically, positions 6, 8, 10, 11, 15 and 17 in the p458 peptide chain (corresponding to positions 463, 465, 467, 468, 472 and 474 of the human HSP60 molecule) can be occupied by either I or L or by other hydrophobic amino acids, natural, such as V, M, or F, or unnatural amino acids, such as norleucine (Nle) or norvaline (Nva). Positions 5, 12, 13 and 16 in the p458h chain (corresponding to positions 462, 469, 470 and 473 of the human HSP60 molecule) can be occupied by either K or R or by unnatural positively charged amino acids, such as ornithine (Orn). Interchange of E and D may also lead to active derivatives.

Accordingly, in one embodiment, the HSP60 peptide is an analog of p458h (SEQ ID NO: 1): $^{458}$NEDQKIGIEI-IKRTLKI$^{474}$ in which the residue E$^{459}$ is either E or D; the residue D$^{460}$ is either D or E; the residue K$^{462}$ is either K or R or ornithine (Orn); the residue I$^{463}$ is either I or L, V, M, F, norleucine (Nle) or norvaline (Nva); the residue I$^{465}$ residue is either I or L, V, M, F, Nle or Nva; the residue E$^{466}$ is either E or D; the residue I$^{467}$ is either I or L, V, M, F, Nle or Nva; the residue I$^{468}$ is either I or L, V, M, F, Nle or Nva; the residue K$^{469}$ is either K or R or Orn; the residue R$^{470}$ is either R, K or Orn; the residue L$^{472}$ in either L or I, V, M, F, Nle or Nva; the residue K$^{473}$ is either K or R or Orn; and the residue I$^{474}$ is either I or L, V, M, F, Nle or Nva.

In certain embodiments, the HSP60 peptide may correspond to a complete HSP60 protein sequence, such as that of E. coli GroEL (gi: 536987; SEQ ID NO: 14); human HSP60 (gi: 49522865; SEQ ID NO: 15), or mouse HSP60 (gi: 31981679; SEQ ID NO: 16).

With respect to the HSP60 peptide, the term "analogs" relates to peptides obtained by replacement, deletion or addition of amino acid residues to the sequence, optionally including the use of a chemically derivatized residue in place of a non-derivatized residue, as long as they have the capability of enhancing substantially the immunogenicity of the Aβ peptide. Analogs, in the case of p458, are peptides such that at least 70%, preferably 90-100%, of the electric properties and of the hydrophobicity of the peptide molecule are conserved. These peptides can be obtained, without limitation, according to the instructions in the paragraph hereinbefore. Ec27 analogs are preferably of at least about 70%, more preferably of at least about 80-90% similarity in their amino acid sequence of Ec27. For example, the corresponding human peptide (Ec27h), having the sequence set forth in SEQ ID NO: 6, exhibits 80% amino acid identity to Ec27.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g. 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g. by the local homology algorithm of Smith and Waterman (1981) Adv Appl Math 2, 482; by the homology alignment algorithm of Needleman and Wunsch (1970) J Mol Biol 48, 443; by the search for similarity method of Pearson and Lipman (1988) Proc Natl Acad Sci USA 85, 2444; by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of a suitable algorithm for determining percent sequence identify and sequence similarity is the BLAST algorithm, which is described in Altschul et al (1990) J Mol Biol 215, 403-410. Software for performing BLAST analyses is publicly available through the National Center or Biotechnology Information (http://www.ncbi.nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff and Henikoff (1989) Proc Natl Acad Sci USA 89, 10915).

For purposes of classifying amino acids substitutions as conservative or nonconservative, amino acids may be grouped in classes according to the following properties: hydrophobic sidechains: norleucine, met, ala, val, leu, ile; neutral hydrophilic side chains: cys, ser, thr; acidic side chains: asp, glu; basic side chains: asn, gin, his, lys, arg; residues influencing chain orientation: gly, pro; and aromatic side chains: tip, tyr, phe. Conservative substitutions involve substitutions between amino acids in the same class. Non-conservative substitutions constitute exchanging a member of one of these classes for a member of another.

In a particular embodiment, the vaccine comprises a covalent conjugate of Aβ1-15 and p458, for example that designated Aβ1-15-p458 (SEQ ID NO: 13). In another embodiment, the vaccine comprises a covalent conjugate of Aβ1-42 and p458, such as that provided by SEQ ID NO: 12. In a particular embodiment, the vaccine comprises a covalent conjugate of Aβ1-15 and p458h, such as that provided by SEQ ID NO: 17.

In other embodiments, the vaccine composition comprises an admixture of peptides. In a particular embodiment, the vaccine composition comprises an admixture of the peptide Aβ1-15 (SEQ ID NO: 9) and the peptide p458h (SEQ ID NO: 1). In a particular embodiment, the vaccine composition comprises an admixture of Aβ1-15 (SEQ ID NO: 9) and p458h (SEQ ID NO: 1).

A vaccine composition may be formulated using one or more pharmaceutically acceptable carriers, excipients or diluents (collectively also known as vehicles). Such formulating substances are "pharmaceutically acceptable" if they are compatible with the other ingredients of the composition and not deleterious to the recipient thereof i.e. substantially free of association with adverse effects. Carriers, excipients and diluents and their use in vaccine compositions are described for example, in Remington's Pharmaceutical Science (15th ed., Mack Publishing Company, Easton, Pa., 1980). Carriers for liquid formulations can include, but are not limited to water, phosphate buffered saline (PBS), Ringer's solution, dextrose solution, serum-containing solutions, Hank's solution, other aqueous physiologically balanced solutions, oils, esters and glycols.

Carriers, excipients and diluents can include substances which function to enhance chemical stability of the active ingredient(s), provide buffering capacity, maintain isotonicity, provide antimicrobial and/or preservative function. Excipients used for buffering include for example, sodium acetate, sodium chloride, sodium lactate, potassium chloride, calcium chloride, and combinations thereof to provide buffers such as phosphate buffered saline (PBS) and bicarbonate buffer. Preservatives include for example, thimerosal, m- and o-cresol, formalin, ETDA and benzethonium chloride. Stabilizers can include for example, glycine, lactose, albumin, sorbitol and monosodium glutamate. Antimicrobial agents can include for example, amphotericin B, polymyxin B, gentamycin, neomycin and streptomycin. The formulations may conveniently be presented in unit dosage form and may be prepared by any method well known in the pharmaceutical art.

Compositions of the invention can include liquid preparations for orifice, e.g., oral, nasal, anal, vaginal, peroral, intragastric, mucosal (e.g., perlinqual, alveolar, gingival, olfactory or respiratory mucosa) etc., administration such as suspensions, syrups or elixirs; and, preparations for parenteral, subcutaneous, intradermal, intramuscular, intraperitoneal or intravenous administration (e.g. injectable administration), such as sterile suspensions or emulsions.

In certain embodiments, intravenous and parenteral administration are preferred. Such compositions may be in admixture with a suitable carrier, diluent, or excipient such as sterile water, physiological saline, glucose, dextrose, glycerol, ethanol or the like and combinations thereof. Typically, such vaccines are prepared as injectables either as liquid solutions or suspensions; solid forms suitable for solution in, or suspension in, liquid prior to injection may also be prepared. The preparation may also be emulsified or lyophilized.

Solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer (1990) Science 249, 1527 and Hanes (1997) Advanced Drug Delivery Reviews 28, 97). The vaccine of the invention can be administered in the form of a depot injection or implant preparation which can be formulated in such a manner as to permit a sustained or pulsatile release of the active ingredient(s) i.e Aβ peptide and HSP60 peptide.

Additional formulations that are suitable for other modes of administration include, but are not limited to, suppositories and oral formulations. For suppositories, traditional binders and carriers may include, for example, polyalkalene glycols or triglycerides. Oral formulations include such normally employed excipients as, for example, pharmaceutical grades of mannitol, cellulose, magnesium carbonate and the like. These compositions take the form of solutions, suspensions, tablets, pills, capsules, sustained release formulations or powders.

The compositions can contain auxiliary substances such as wetting or emulsifying agents, pH buffering agents, gelling or viscosity enhancing additives, preservatives, flavoring agents, colors, and the like, depending upon the route of administration and the preparation desired.

In certain preferable embodiments, the vaccine compositions of the invention do not comprise an additional adjuvant.

In alternate embodiments, the vaccine compositions of the invention may further comprise a pharmaceutically acceptable adjuvant, When an adjuvant is included, it is preferably one which is not associated with Th-17 responses, such as an aluminum-based adjuvant, also known as "alum". Such adjuvants include aluminum hydroxide, aluminum phosphate and aluminum potassium sulfate, as is known in the art. Additional adjuvants include, but are not limited to, oils or emulsions thereof, such as incomplete Freund's adjuvant, surface active substances, e.g., hexadecylamin, octadecyl amino acid esters, octadecylamine, lysolecithin, dimethyl-dioctadecylammonium bromide, N,N-dicoctadecyl-N'—N'bis(2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions (including, but not limited to, oil-in-water emulsions having oil droplets in the submicron range, such as those disclosed by U.S. Pat. Nos. 5,961,970, 4,073,943 and 4,168,308); liposaccharides such as MPL® and mineral gels. The conjugates of this invention can also be incorporated into liposomes, cochleates, biodegradable polymers such as polylactide, poly-glycolide and poly-lactide-co-glycolides, or ISCOMS (immunostimulating complexes), and supplementary active ingredients may also be employed.

The vaccine composition can be administered to a human or animal by a variety of routes, including but not limited to parenteral, intradermal, transdermal (such as by the use of slow release polymers), intramuscular, intraperitoneal, intravenous, subcutaneous, oral and intranasal routes of administration, according to protocols well known in the art. The particular dosage of the Aβ peptide antigen will depend upon the age, weight and medical condition of the subject to be treated, as well as the method of administration. Suitable doses will be readily determined by the skilled artisan. An exemplary dose of Aβ peptide for human intramuscular, subcutaneous and oral vaccination is between about 0.1 and about 1000 µg. Adjustment and manipulation of established dosage ranges used with traditional carriers for adaptation to the present vaccine composition is well within the ability of those skilled in the art.

Peptide Synthesis

The individual peptides or the covalent conjugate comprising the vaccine composition of the invention may be synthesized using any recombinant or synthetic method known in the art, including, but not limited to, solid phase (e.g. Boc or f-Moc chemistry) and solution phase synthesis methods.

The amino acid residues described herein are preferred to be in the "L" isomeric form. However, residues in the "D" isomeric form can be substituted for any L-amino acid residue, as long as the peptide substantially retains the desired functional property. Use of "D" amino acids may be used as is known in the art to increase the stability or half-life of the resultant peptide.

Reference herein to p458, p458h and Ec27 peptides also encompasses salts and functional derivatives thereof, as long as they are able to substantially enhance the immunogenicity of the Aβ peptide. Similarly, reference herein to Aβ peptides also encompasses salts and functional derivatives thereof, as long as they are able to illicit an immune response directed against Aβ1-42 or a fragment thereof Thus, the present invention encompasses peptides containing non-natural amino acid derivatives or non-protein side chains.

The term derivative includes any chemical derivative of the peptides of the invention having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide or conjugate can differ from the natural sequence of the polypeptides or peptides of the invention by chemical modifications including, but not limited to, terminal-NH$_2$ acylation, acetylation, or thioglycolic acid amidation, and by terminal-carboxlyamidation, e.g. with ammonia, methylamine, and the like. Peptides can be either linear, cyclic or branched and the like, which conformations can be achieved using methods well known in the art.

It is noted that both shorter active fragments and longer peptides comprising the disclosed Aβ peptide sequences and HSP60 epitopes are within the scope of the present invention. Such fragments or peptides may be comprise, for example, peptides having 1-3 amino acids deleted at either termini, or addition of 1-3 amino acid residues or more from the flanking sequences of the viral protein to either termini, as long as their ability to elicit an immune response according to the principles of the invention is retained. It is to be understood that longer peptides, e.g. up to 50 amino acids in length may also be used for vaccination according to the invention. However, shorter peptides may be preferable for being easier to manufacture and/or administer.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

The conjugates of the invention may be created by chemically crosslinking an Aβ peptide with an HSP60 epitope, such as an p458 or Ec27 peptide, using methods well known in the art. Such crosslinking methods include the formation of disulfide linkages using N-succinimidyl-3-(2-pyridyl-thio) propionate (SPDP) and succinimidyl 4-(N-maleimidomethyl) cyclohexane-1-carboxylate (SMCC) (if the peptide lacks a sulfhydryl group, this can be provided by addition of a cysteine residue). These reagents create a disulfide linkage between themselves and peptide cysteine resides on one peptide and an amide linkage through the s-amino on a lysine, or other free amino group in other amino acids. A variety of disulfide/amide-forming agents are described in Immun Rev 62, 185 (1982). Other bifunctional coupling agents form a thioether rather than a disulfide linkage. Such thioether forming agents include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

The peptides of the invention may be formulated into the vaccine composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

The invention further encompasses methods for preparing the vaccine composition. In the case of a composition comprising an admixture, the Aβ peptide and the HSP60 peptide may be individually synthesized, purified and thereafter combined and formulated together with appropriate carrier, excipient or diluent, as hereinbefore described. For a composition comprising a covalent conjugate, said conjugate may be prepared as hereinbefore described, and thereafter combined and formulated with a appropriate carrier, excipient or diluent.

Liposomes

In a particular embodiment, the active components of the invention may be formulated in liposome carriers. Accordingly, the composition may be in the form of liposomes.

Liposomes comprise liposome-forming lipids (also referred to as "vesicle-forming lipids") which are characterized by a hydrophilic tail and a hydrophobic and polar head group moiety, which can spontaneously form bilayer vesicles in water. Liposome-forming lipids are stably incorporated in lipid bilayers such that the hydrophobic moiety is in contact with the interior region of the vesicle membrane while the polar head group moiety is oriented to the exterior, polar surface of the vesicle membrane.

In a particular embodiment, the Aβ peptide and the HSP60 peptide are co-encapsulated within the same liposome preparation. In this case, the Aβ peptide and the HSP60 peptide may be present in the liposome as an admixture or as a covalent conjugate. In contrast, the Aβ peptide and the HSP60 peptide may be separately encapsulated within different liposome preparations. In a particular embodiment, the Aβ peptide and the HSP60 peptide are displayed on the outer surface of the liposome. In one embodiment a covalent conjugate of the Aβ peptide and the HSP60 peptide is displayed on the outer surface of the liposome. In a particular embodiment, the liposomes comprise an Aβ peptide encapsulated therein and an HSP60 peptide displayed on the outer surface of the liposome. In a particular embodiment, the liposomes comprise an HSP60 peptide encapsulated therein and an Aβ peptide displayed on the outer surface of the liposome. In particular embodiments, the liposomes comprise a complete HSP60 protein sequence, such as that of E. coli GroEL (SEQ ID NO: 14); human HSP60 (SEQ ID NO: 15), or mouse HSP60 (SEQ ID NO: 16). In a particular embodiment, the liposomes comprise a covalent conjugate comprising a sequence selected from SEQ ID NO: 13 and SEQ ID NO: 17.

A variety of liposomal forming lipids can be used, as disclosed for example in U.S. Pat. No. 5,919,480. The lipids or oily vesicle forming substances allow long-term storage of the liposome-encapsulated peptides and effective release of these components upon administration. Representative lipids include, but are not limited to, dimyristoyl phosphatidylcholine (DMPC), dimyristoyl phosphatidylglycerol (DMPG), cholesterol, 1,2-distearoyl-3-trimethylammonium propane (DSTAP), 1,2-dimyristoyl-3-trimethylammonium propane (DMTAP), and combinations thereof, such as DMPC/cholesterol, DMPC/DMPG, DMPC/DMPG/cholesterol, DMPC/DMTAP, and DMPG/DMTAP/cholesterol.

Liposomes may be prepared by a variety of techniques. To form multilamellar vesicles (MLV), a mixture of vesicle-forming lipids is dissolved in a suitable organic solvent (or solvent mixtures), for example tert-butanol, and evaporated in a vessel to form a thin film, which is then hydrated by an aqueous medium to form lipid vesicles, typically in sizes ranging from about 0.1 to about 10 μm. The lyophilized MLV preparation can be resolubilized as an aqueous suspension. The MLV suspension can then be selectively downsized to a desired vesicle size range e.g. 1 micron or less, by extruding aqueous suspension through a polycarbonate membrane having a select uniform pore size, typically 0.05 to 1.0 microns.

Phospholipids may spontaneously form vesicles in an aqueous environment or are stably incorporated into lipid bilayer membranes with the hydrophobic portion of the lipid molecule in the interior and the polar head group portion of the lipid molecule in the hydrophilic, external surface of the bilayer vesicle. The lipid bilayer membrane of the liposomal vesicle is suitable for holding the hydrophilic peptides within and on the lipoid membrane vesicle enclosure.

Vesicle-forming lipids may include hydrocarbon chains, a steroid group, or a chemically reactive group, such as acid, alcohol, aldehyde, amine or ester, as a polar head group. The phospholipids include vesicle forming combinations of phosphatidic acid (PA), phosphatidyl choline (PC), phosphatidyl ethanolamine (PE), phosphatidyl glycerol, phosphatidyl inositol (PI), and sphingomyelin (SM) which generally comprise two hydrocarbon chains of about 14-22 carbons at varying degrees of unsaturation. Lipopolymers can be added to stabilize the lipid content of the vesicles. Furthermore, vesicles can be formed from glycolipids, including cerebrosides and gangliosides, as well as sterols (i.e. cholesterol). Synthetic membrane forming phosphatidyl derivative compounds containing dihexadecyl, dioleoyl, dilauryl, dimyristoyl, or dipalmitoyl groups are also available (Calbiochem), including dimyristoyl phosphatidyl choline or dimyristoyl phosphatidyl glycerol which can be taken as a mixture, with and without lipid membrane stabilizing additives.

Various methods are available for encapsulating peptides and additional agents in the liposomes. For example, in the reverse phase evaporation method (Szoka, U.S. Pat. No. 4,235,871) a non-aqueous solution of vesicle-forming lipids is dispersed with a smaller volume of an aqueous medium to form a water-in-oil emulsion. Thus, for encapsulation the active ingredients or agents are included either in the lipid solution, in the case of a lipophilic agent, or in the aqueous medium, as in the case of a water-soluble agent. After removal of the lipid solvent, the resulting gel is converted to liposomes. These reverse phase evaporation vesicles (REVs) have typical average sizes from about 2 to about 4 microns and are predominantly oligolamellar, that is, containing more than one or at least a few lipid bilayer shells. The REVs may be sized by extrusion, to give oligolamellar vesicles having e.g. a maximum selected size between about 0.05 and about 1.5 µm.

Preparations of large multilamellar vesicles (LMLV) or REV can be further treated, e.g., by way of extrusion, sonication or high pressure homogenization, to produce small unilamellar vesicles (SUV's), which are characterized by sizes in the range of about 0.03 micron to about 0.1 micron. Alternatively, SUV's can be formed directly by homogenization of an aqueous dispersion of lipids.

Other methods for adding additional components to liposomal compositions include methods wherein an aqueous liposome dispersion is co-lyophilized with other components and the resulting solid redispersed to form MLV. Another method (A. Adler, Cancer Biother. 10: 293, 1995) provides addition of an aqueous solution of the agent to be encapsulated to a t-butanol solution of lipids. The mixture is sonicated and lyophilized, and the resulting powder is rehydrated.

Liposome compositions containing an entrapped agent can again be treated after final sizing, if necessary, to remove the free (non-entrapped) agent. Conventional separation techniques, such as centrifugation, diafiltration, and ultrafiltration are suitable for this purpose.

The composition can also be sterilized by filtration through a conventional 0.45 micron filter. In order to form the compositions of the current invention, the concentration of peptides in the liposomes can be chosen to give a protein/lipid molar ratio from about 1:100 to about 1:1000, at 100% encapsulation, after filtration.

Stabilizers may also be added to the liposomal compositions, for example, a metal chelator. For more extended storage, the compositions may be converted to a dry lyophilized powder, and can be hydrated to form an aqueous suspension as needed before use.

The vaccine composition may further comprise micelles. As used herein, "micelles" refers to any water soluble aggregate which is spontaneously and reversibly formed from amphiphilic compounds or ions. Lipids, in particular phosphatidyl glycerol lipid derivatives are useful for forming micelles. Representative examples include dipalmitoyl phosphatidyl glycerol, dimyristoyl phosphatidyl glycerol, and dicapryl phosphatidyl glycerol. Micelles suitable for use in the invention are disclosed for example in U.S. Pat. Nos. 7,332,527 and 7,413,538.

Nucleic Acids and Recombinant Techniques

In certain embodiments, the peptides of the invention are prepared using recombinant methods well know in the art (see e.g. Sambrook et al, (2001) *Molecular Cloning: A Laboratory Manual*).

For example, production of a complete HSP60 protein sequence will typically utilize a DNA molecule encoding a HSP60 protein, with the DNA molecule being linked in frame with suitable regulatory elements. For production of a conjugate, including multimeric conjugates, a DNA molecule encoding an HSP60 peptide (either a single copy or multiple copies in tandem) may be linked in frame to a DNA molecule encoding an Aβ peptide (either a single copy or multiple copies in tandem). The encoded peptide or polypeptide comprises multiple peptide units, which may be linked directly or via a linker. Accordingly, the invention further provides nucleic acid molecules encoding Aβ peptides, HSP60 peptides and peptide conjugates of the invention.

The nucleic acid molecules utilized to produce the Aβ peptides, HSP60 peptides and peptide conjugates may include DNA, RNA, or derivatives of either DNA or RNA. An isolated nucleic acid sequence encoding an Aβ peptide or a HSP60 peptide, including a full length HSP60 protein sequence, can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

A nucleic acid molecule homolog can be produced using a number of methods known to those skilled in the art (see, for example, Sambrook et al., 2001). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the protein encoded by the nucleic acid with respect to the induction of an anti-viral response, for example by the methods described herein.

A polynucleotide or oligonucleotide sequence can be deduced from the genetic code of a protein, however, the degeneracy of the code must be taken into account. Nucleic acid sequences of the invention also include sequences, which are degenerate as a result of the genetic code, which sequences may be readily determined by those of ordinary skill in the art.

The oligonucleotides or polynucleotides of the invention may contain a modified internucleoside phosphate backbone to improve the bioavailability and hybridization properties of the oligonucleotide or polynucleotide. Linkages are selected from the group consisting of phosphodiester, phosphotriester, methylphosphonate, phosphoroselenoate, phosphorodiselenoate, phosphoroanilothioate, phosphoroanilidate, phosphoramidate, phosphorothioate, phosphorodithioate or combinations thereof.

Additional nuclease linkages include alkylphosphotriester such as methyl- and ethylphosphotriester, carbonate such as carboxymethyl ester, carbamate, morpholino carbamate, 3'-thioformacetal, silyl such as dialkyl (C1-C6)- or diphenylsilyl, sulfamate ester, and the like, as is known in the art.

The present invention includes a nucleic acid sequence of the present invention operably linked to one or more transcription control sequences to form a recombinant molecule. The phrase "operably linked" refers to linking a nucleic acid sequence to a transcription control sequence in a manner such that the molecule is capable of being expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, insect cells, and animal cells.

A nucleic acid molecule of the invention may be inserted into appropriate expression vector, i.e., a vector which contains the necessary elements for the transcription and translation of the inserted coding sequence.

Vectors can be introduced into cells or tissues by any one of a variety of known methods within the art, including in vitro recombinant DNA techniques, synthetic techniques, and in vivo genetic recombination. Such methods are generally described in Sambrook et al., (2001), in Ausubel et al., Current Protocols in Molecular Biology, John Wiley and Sons, Baltimore, Md. 1989.

A recombinant cell of the present invention comprises a cell transfected with a nucleic acid molecule that encodes a viral antigen of the invention. A variety of expression vector/host systems may be utilized to contain and express sequences encoding the viral antigens of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed. The expression of the construct according to the present invention within the host cell may be transient or it may be stably integrated in the genome thereof.

Host cells transformed with nucleotide sequences encoding a peptide or protein of the invention may be cultured under conditions suitable for the expression and recovery of the protein from cell culture. The protein produced by a transformed cell may be secreted or contained intracellularly depending on the sequence and/or the vector used. The fusion protein may also be designed to include a purification facilitating domain, optionally linked to the fusion protein via a cleavable linker sequence, such as those specific for Factor XA or enterokinase (Invitrogen, San Diego, Calif.). Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.).

Methods of Treatment and Prevention

The invention further provides a method for preventing and treating neurological disorders associated with Aβ plaque accumulation, the method comprising the step of administering to a subject in need thereof with a therapeutically effective amount of the composition of the invention.

The method may be applied to a subject having a known genetic risk of developing AD. Such individuals include those having relatives afflicted with AD, and those whose risk is determined by analysis of genetic or biochemical markers. Genetic markers of risk toward AD include mutations in the APP gene, particularly mutations at position 717 and positions 670 and 671 referred to as the Hardy and Swedish mutations respectively (see Hardy, supra). Other markers of risk are mutations in the presenilin genes, PS1 and PS2, and ApoE4, hypercholesterolemia or atherosclerosis. Individuals presently suffering from AD can be recognized from characteristic dementia, as well as the presence of risk factors described above. In addition, a number of diagnostic tests are available for identifying individuals who have AD. These involve measurement of CSF tau and Aβ1-42 levels.

The method of the invention may also be applied to subjects having Down's syndrome, since these individuals are at risk of developing AD-like neurological manifestations with age.

According to the invention, a therapeutically effective amount of the composition is sufficient to substantially reduce the severity or progression of the disease, or to substantially prevent appearance of signs and symptoms of the disease. In the case of AD, signs and symptoms include behavioural and cognitive defects, as well as neuropathological lesions, such as Aβ plaque accumulation.

The composition is typically administered in several dosages over prolonged periods until a sufficient immune response has been achieved. Typically, the immune response i.e. of serum antibodies, is monitored and repeated dosages are given if the immune response starts to fade.

A therapeutically effective amount may vary among individuals, depending upon many different factors, including means of administration, target site, physiological state of the patient, the species of the subject, other medications administered, and whether treatment is prophylactic or therapeutic. The subject is generally a human, but may also be a nonhuman mammal. Treatment dosages need to be titrated to optimize safety and efficacy. The amount of the composition i.e. the combination of the Aβ peptide and the HSP60 peptide, whether prepared as an admixture or as a conjugate, may depend on the molar ratio between these two components, since a composition with a relatively higher ratio of HSP60 peptide to Aβ peptide may induce a high level of antibody production. A suitable amount of Aβ peptide immunogen for administration may be in the range from 1 μg-500 μg per patient and more usually from 5-500 μg per dose (typically by injection) for human administration. A higher dose of 1-2 mg per injection may be used. Typically about 10, 20, 50 or 100 μg is used for each human injection. The timing of injections can vary significantly from once a day, to once a year, to once a decade. On any given day that a dosage of Aβ peptide immunogen is given, the dosage is greater than 1 μg/patient and usually greater than 10 μg/patient, and often greater than 100 μg/patient.

In particular embodiment, the composition is administered in an amount of 0.1 to 3 mg/ml, for example in an amount of 1 mg/ml. A typical administration regimen consists of an initial vaccinating dose followed by subsequent i.e. "booster" injections at regular intervals, for example, at 6 weekly intervals. Another regimen consists of an initial dose followed by booster injections 1, 2 and 12 months later. Another regimen entails administration of a dose e.g. by injection, every two months for life. In another embodiment, the composition is administered at regular intervals over a period of one month to two years. The regular intervals can be from once a week to once every four weeks.

Alternatively, booster injections can be on an irregular basis as indicated by monitoring of immune response.

Doses for nucleic acids encoding immunogens range from about 10 ng to 1 g, 100 ng to 100 mg, 1 μg to 10 mg, or 30-300 μg DNA per patient. Doses for infectious viral vectors vary from $10\text{-}10^{-9}$ or more, virions per dose.

The vaccine may be administered by intramuscular; intravenous; intradermal; transcutaneous; intranasal, oral, intraperitoneal and subcutaneous means.

The composition of the invention can optionally be administered in combination with other agents that increase passage of the agents of the invention across the blood-brain barrier.

The method may further involve assaying the level of anti-Aβ1-42 antibodies in the serum of the subject prior to and following administration of the composition in order to assess the immune response. Conveniently, the assaying may comprise use of an ELISA technique, or any other similar technique known in the art to identify and quantify serum antibodies.

For example, in a suitable ELISA technique, Aβ1-42 is coated onto the walls of 96-well microtiter plates. Serial dilutions of serum obtained from a subject are added to the wells and incubated under appropriate conditions to allow specific antigen-antibody binding. The reacted serum is washed away and a first known antibody having specificity for the Fc portion of human IgG, e.g. goat anti-human IgG, conjugated with an enzyme (e.g. horseradish peroxidase, alkaline phosphatase, glucose oxidase, or β-galactosidase) is added to the wells and incubated under appropriate conditions to allow specific binding. After washing, appropriate enzyme substrate is added and the colorometric reaction is quantified in a dedicated sample reader. For a more sensitive sandwich assay, the enzyme may be conjugated to a second known antibody having specificity for the first known antibody.

The method of the invention may further comprises assessing the level of cognitive function in the subject prior to and following the step of administering the composition, wherein an improvement in the level of cognitive function is indicative of the efficacy of the method.

In another aspect of the invention, there is provided a use of an isolated Aβ peptide and an isolated HSP60 peptide for the preparation of a therapeutic composition for the prevention and/or treatment of a neurological disorder associated with Aβ plaque accumulation.

REFERENCES

Agadjanyan et al (2005) J Immunol 174, 1580-86.
Anderton et al (1993) Eur J Immunol 23, 33-38.
Bard et al (2003) Proc Nat Acad Sci 100, 2023-2028.
Barrios et al (1992) Eur J Immuol 22, 1365-72.
Cribbs et al (2003) Int Immunol 15, 505-514.
Cummings (2004) N Engl J Med 351, 56-67.
Dodart et al (2002) Nat Neurosci 5, 452-457.
Ferrer et al (2004) Brain Pathol 14, 11-20.
Ghochikyan et al (2003) Eur J Immunol 33, 3232-41.
Gilman et al (2005) Neurology 64, 1553-62.
Hardy et al (1997) Trends Neurosci 20, 154-159.
Hermann et al (1991) Eur J Immunol 21, 2139-2143.
Hock et al (2003) Neuron 38, 547-554.
Jindal et al (1989) Mol Cell Biol 9, 2279-2283.
Kim et al (2007) Immunol Lett 112, 30-38.
Koga et al (1989) Science 245, 1112-1115.
Konen-Waisman et al (1999) J Infect Dis 179, 403-413.
Konen-Waisman et al (1995) 154, 5977-5985.
Maier et al (2006) J Neurosci 26, 4717-4728.
Monsonego et al (2003) J Clin Invest 112, 415-422.
Monsonego et al (2006) Proc Nat Acad Sci 103, 5048-53.
Monsonego et al (2001) Proc Nat Acad Sci 98, 10273-78.
Morgan et al (2000) Nature 408, 982-985.
Nicoll et al (2003) Nat Med 9, 448-52.
Nicoll et al (2006) J Neuropathol Exp Neurol 65, 1040-8.
Petrushina et al (2007) J Neurosci 27, 12721-31.
Qu et al (2004) Arch Neurol 61, 1859-64.
Schenk et al (1999) Nature 400, 173-177.
Schneider et al (2003) Am J Geriatr Psychiatry 11, 414-425.
Takeda et al (2006) Int J Geriatr Psychiatry 21, 17-28.

The foregoing description of the specific embodiments will so fully reveal the general nature of the invention that others can, by applying current knowledge, readily modify and/or adapt for various applications such specific embodiments without undue experimentation and without departing from the brand concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Ex Vivo Proliferation of HSP-Specific T Cells in SJL and DRB1-1501 Transgenic Mice Mice (C57BL6, SJL, and DRB1-1501 transgenic (Tg) mice) were vaccinated with p458 (1 mg/ml) emulsified in in complete Freund's adjuvant (IFA) and 10 days later lymph node-derived T cells were stimulated in culture [5×10$^5$ cells/well (U-bottom 96-well plate)] with increasing concentrations of p458. Three days later H$^3$-thymidine incorporation was measured. As shown in FIG. 1, antigen-specific T-cell proliferation was induced in SJL mice and humanized HLA DRB1-1501 Tg mice but not in C57BL6 mice.

Example 2

Aβ Specific Antibodies in SJL Mice Vaccinated with Aβ1-15-p458 Conjugate

Figure 2:
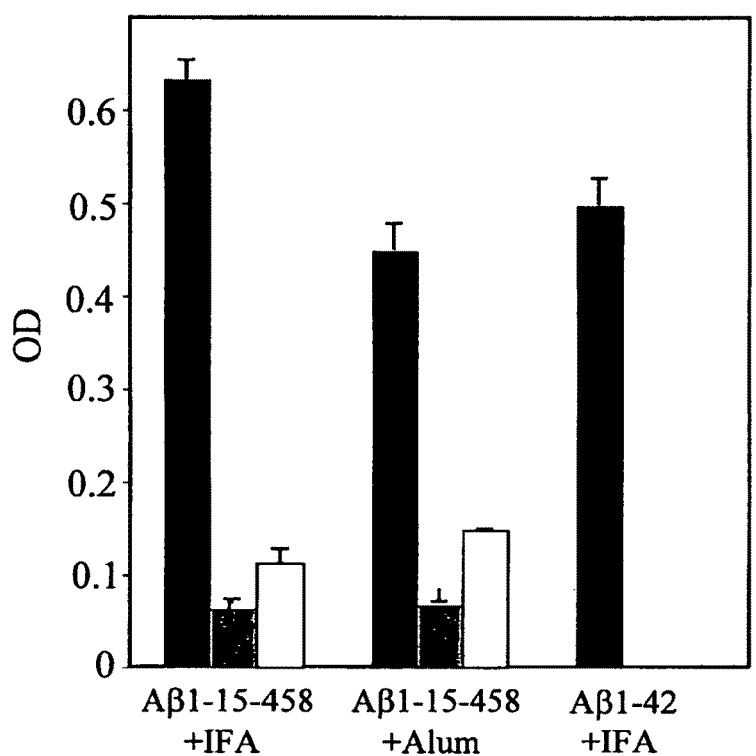
FIG. 2 illustrates the induction of Aβ specific antibodies in SJL mice following vaccination with an Aβ1-15-p458 conjugate (SEQ ID NO: 13), abbreviated as Aβ1-15-458, in incomplete Freund's adjuvant (IFA) or Alum, or vaccination with Aβ1-42 in IFA. Levels of IgG1 (black bars); IgG2a (gray bars) and IgG2b (white bars) are shown.

SJL mice (3 mice/group) were vaccinated with the chimeric peptide Aβ1-15-p458 (1 mg/ml) emulsified in Alum or IFA or with Aβ1-42 emulsified in IFA. Mice were then boosted twice with the same emulsions in 2-week intervals and antibodies to Aβ were measured by ELISA. Titers of Aβ-specific antibodies were similar in sera from mice immunized with Aβ1-15-p458 as compared with sera derived from Aβ1-42 vaccinated mice (FIG. 2). Primarily the IgG1 isotype was detected in all mice (FIG. 2).

Example 3

Aβ1-15-p458 Immunization Induces the Production of Aβ Antibodies in APP Tg Mice

Figure 3:
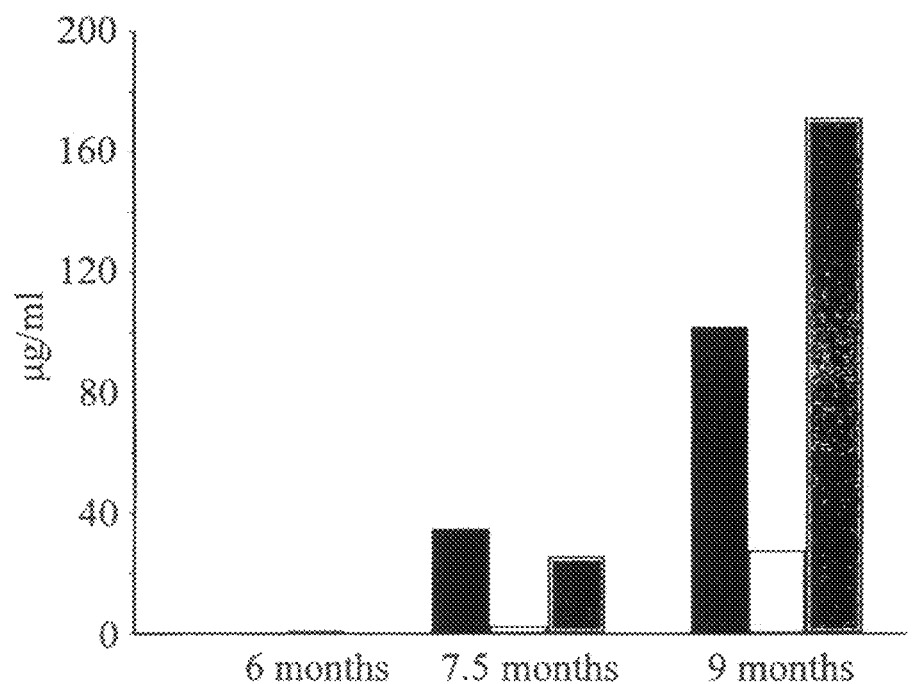
FIG. 3 illustrates the induction of Aβ specific antibodies in amyloid precursor protein (APP) Tg mice (B6SJLF1) following vaccination with Aβ1-15-p458. Levels of IgG1 (black bars); IgG2a (white bars) and IgG2b (gray bars) at the indicated time points post-vaccination are shown.

Amyloid precursor protein (APP) Tg mice (B6SJLF1) were vaccinated with Aβ1-15-p458 emulsified with IFA at 5 months of age and every three weeks thereafter. IgG1, IgG2a, and IgG2b antibodies specific to Aβ1-42 were measured by sandwich ELISA at 6, 7.5, and 9 months of age according to manufacture's instructions. At nine months of age, animals were given deep anesthesia with an overdose of pentobarbital and then cardially perfused with 10 ml of PBS. The results demonstrate increasing concentrations of Aβ antibodies in sera of APP-Tg mice after each immunization, reaching about 170 μg/ml 2 weeks after the last boost (FIG. 3). Both IgG1 and IgG2b were observed throughout the experiment with only limited amounts of IgG2a (FIG. 3), suggesting that a Th2 type of immune response was induced.

Example 4

Aβ1-15-p458 Immunization Induces Clearance of Aβ in Mouse Models of AD

Figure 4:
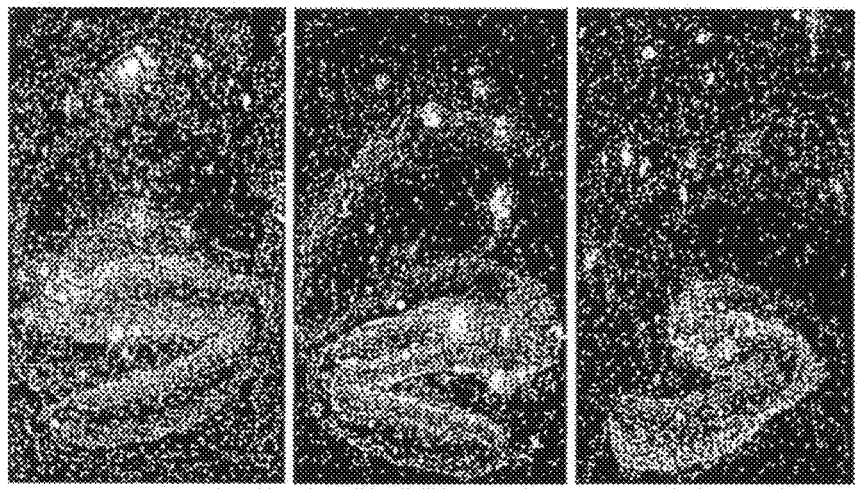
FIG. 4 illustrates clearance of Aβ plaques from brain in different APP Tg mice following vaccination with Aβ1-15-p458 (lower panels), as compared with non-vaccinated mice (upper panels).
Figure 4:
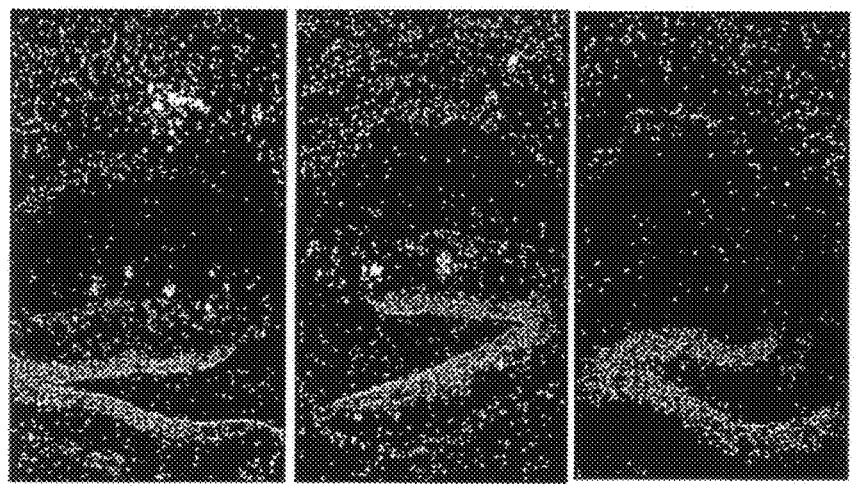
Figure 5:
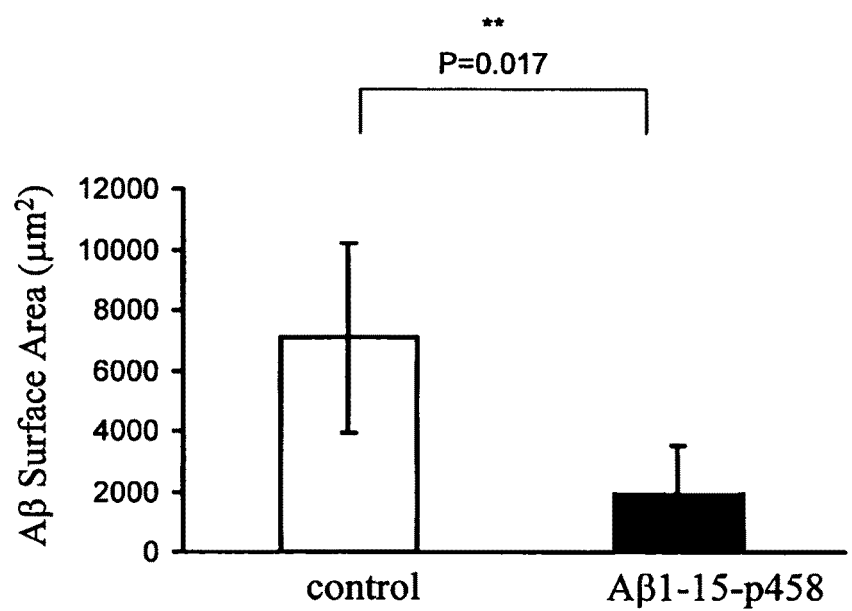
FIG. 5 illustrates stereological quantification of Aβ plaques in APP Tg mice following vaccination with Aβ1-15-p458 (black bars) and in non-vaccinated APP Tg mice (white bars).

Brain sections (at least 3) of mice immunized with Aβ1-15-p458 and of control non-immunized mice were fixed with 4% paraformaldehyde and immunolabeled with Aβ antibodies followed by second staining with Alexa 488 fluorescent antibodies. Slices were counterstained with TO-PRO-3 iodide (642/661) (Invitrogen) and all images were obtained using an Olympus FluoView FV 1000 confocal microscope (Olympus, Germany). As shown in FIG. 4, robust Aβ staining was observed in brain sections of control non-immunized mice (upper panels) whereas only limited Aβ plaques were observed in Aβ1-15-p458 immunized APP Tg mice (lower panels). The Aβ antibodies generated following Aβ1-15-p458 vaccination were capable of preventing amyloid plaque production and/or enhanced its clearance from the brain of APP-Tg mice. Stereological quantification of Aβ staining in brain sections of APP-Tg mice revealed significantly lower amounts of Aβ in immunized mice as compared to control mice (FIG. 5).

Figure 6:
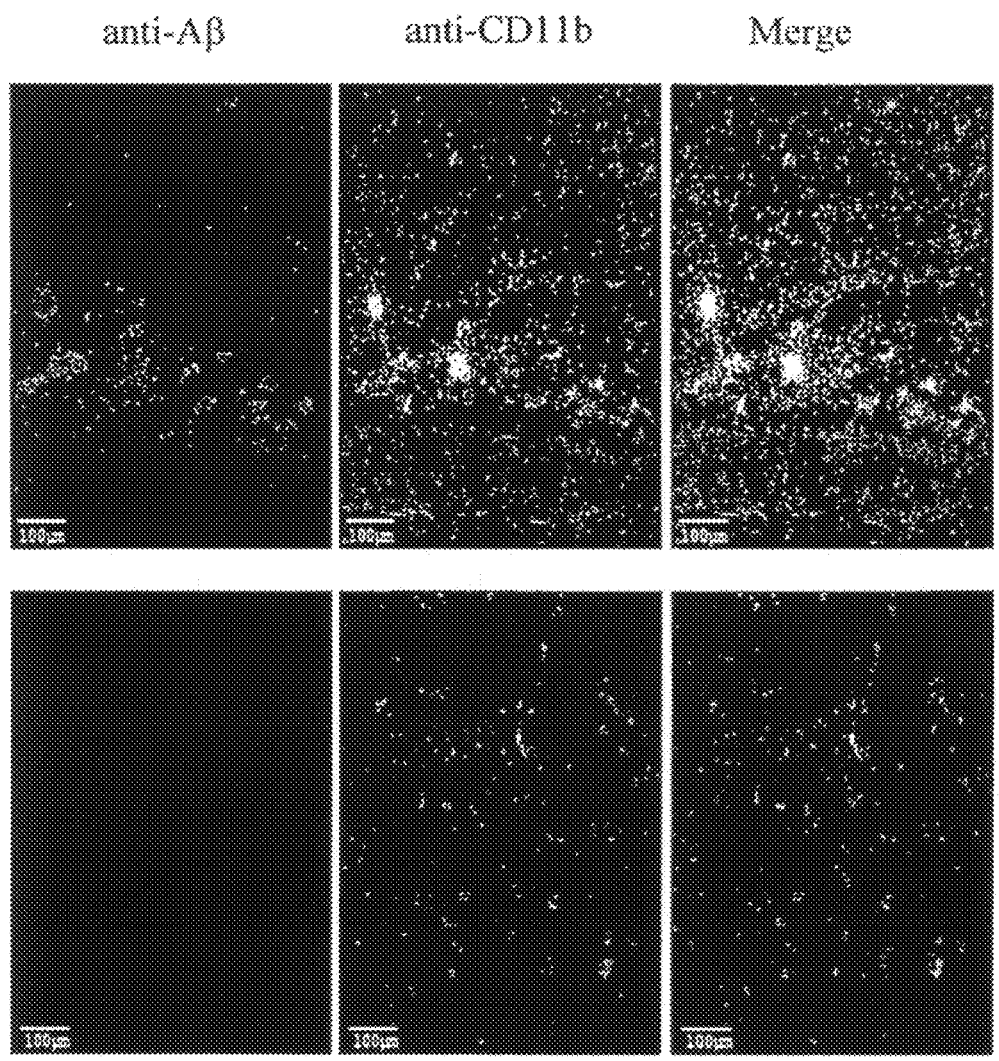
FIG. 6 illustrates that clearance of Aβ plaques was associated with reduced glial activation in APP Tg mice following vaccination with Aβ1-15-p458 (lower panels), but not with control mice vaccinated with adjuvant alone (upper panels). Brain sections were immunolabeled with antibodies to Aβ (anti-Aβ) and the microglia cell marker CD11b (anti-CD11b) and counterstained with TO-PRO-3 iodide.

To determine whether immunization-induced clearance of Aβ was associated with reduced glial activation, brain sections were immunolabeled with antibodies to Aβ and the microglia cell marker CD11b. Slices were counterstained with TO-PRO-3 iodide. As shown in FIG. 6 (upper panels), brain sections from non-immunized APP Tg mice show robust accumulation of Aβ plaques primarily at the hippocampus colocalized with microglia activation. The absence of Aβ plaques in Aβ1-15-p458 immunized mice resulted in a significant decrease in microglial activation (FIG. 6, lower panels).

Example 5

Figure 7:
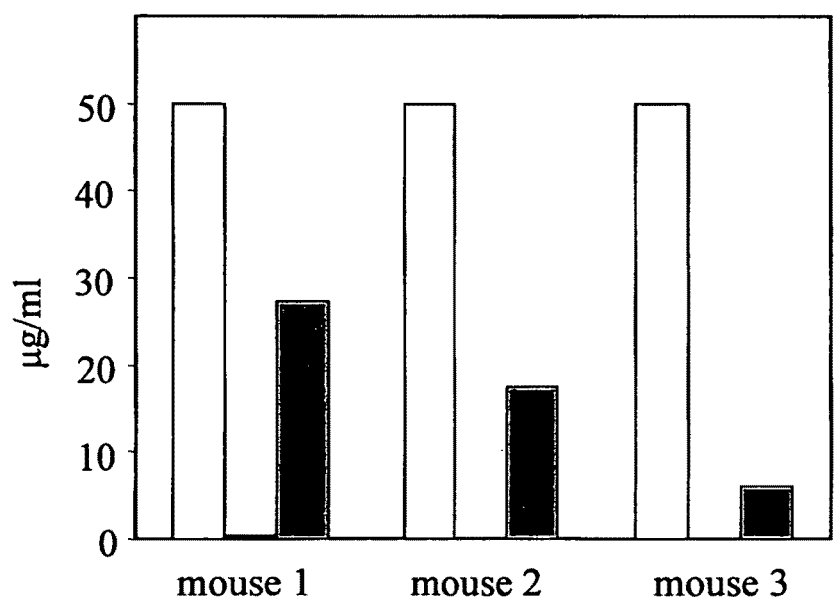
FIG. 7 illustrates the induction of Aβ specific antibodies in three different humanized HLA DR15/APP Tg mice following vaccination with Aβ1-15-p458. Levels of IgG1 (white bars); IgG2a (black bars) and IgG2b (gray bars) are shown.

Aβ1-15-p458 Immunization Induces the Production of Aβ Antibodies in Humanized HLA DR15/APP Tg Mice APP/HLA DR15 mice (i.e. progeny of APP Tg mice crossed with humanized HLA-DR15 mice) were immunized with Aβ1-15-p458. As shown in FIG. 7, IgG1 and IgG2b isotypes were induced following immunization, suggesting a Th2 type of immunization, similar to that observed in APP Tg mice.

Figure 8:
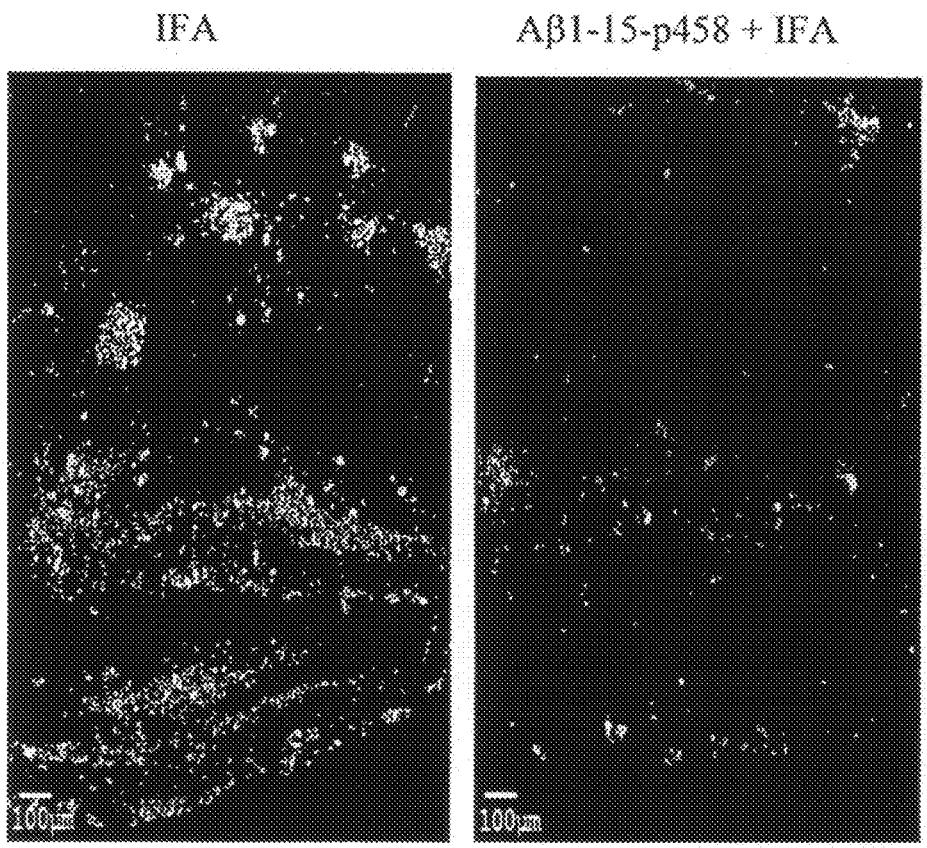
FIG. 8 illustrates clearance of Aβ plaques from brain in humanized HLA DR15/APP Tg mice following vaccination with Aβ1-15-p458 in IFA (right panel), but not in control mice vaccinated with IFA alone (left panel).

APP/HLA DR15 mice were then immunized at 5 months of age and every 3 weeks thereafter. At 10 months of age, mice were killed and analyzed for clearance of Aβ from the brain by immunohistochemistry. FIG. 8 demonstrates a representative brain section from a mouse immunized with Aβ1-15-p458 emulsified in IFA (right panel) and that from a control IFA immunized mouse (left panel). As shown, Aβ1-15-p458 immunization induced significant clearance of Aβ from the brain of HLA-DR15 APP Tg mice.

Example 6

Groups of APP/HLA-DR15 Tg mice were vaccinated with either Aβ1-15-p458 or Aβ1-42 at different doses, according to a schedule of initial injection and three boosts. Following completion of the vaccination schedule, splenic T cells were harvested and assayed for the T cell responses of T cell proliferation, interferon-gamma (IFN-γ) secretion and interleukin-2 (IL-2) secretion.

Figure 9A:
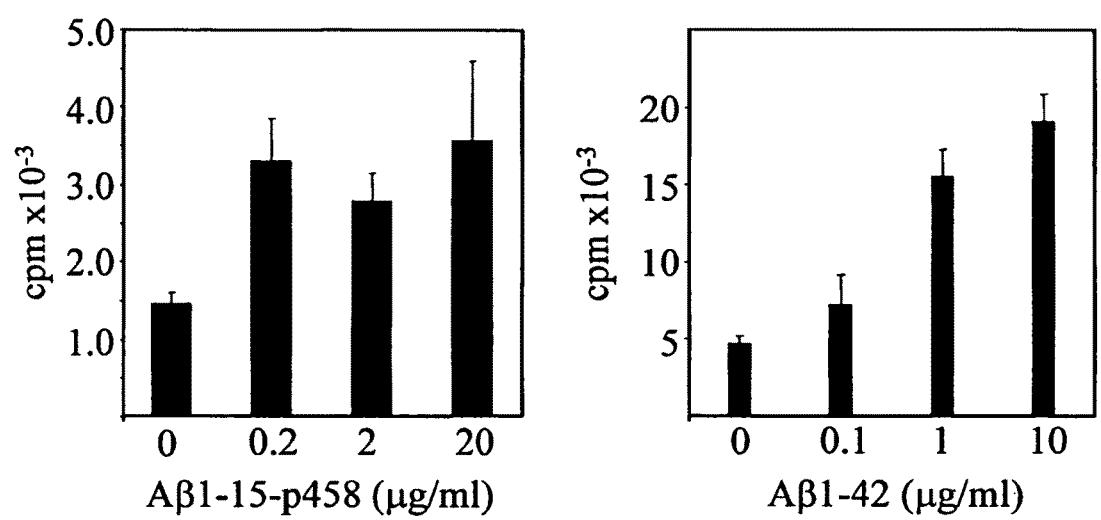
FIG. 9A, T cell proliferation.

As shown in FIG. 9A, HSP-specific T cell proliferation was significantly lower in cells from Aβ1-15-p458 vaccinated mice (left panel), as compared to cells from Aβ1-42 vaccinated mice (right panel).

Figure 9B:
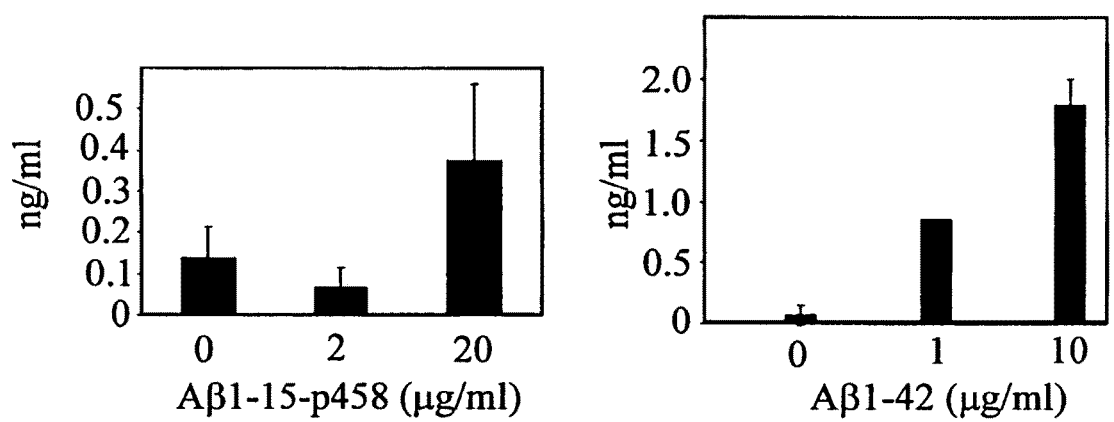
FIG. 9B, Interferon-gamma secretion.

FIG. 9B shows that the HSP-activated T cells from Aβ1-15-p458 vaccinated mice produced a significantly lower concentration of IFN-γ (Th1 cytokine), as compared to that from Aβ1-42 vaccinated mice (left panel vs. right panel).

Figure 9C:
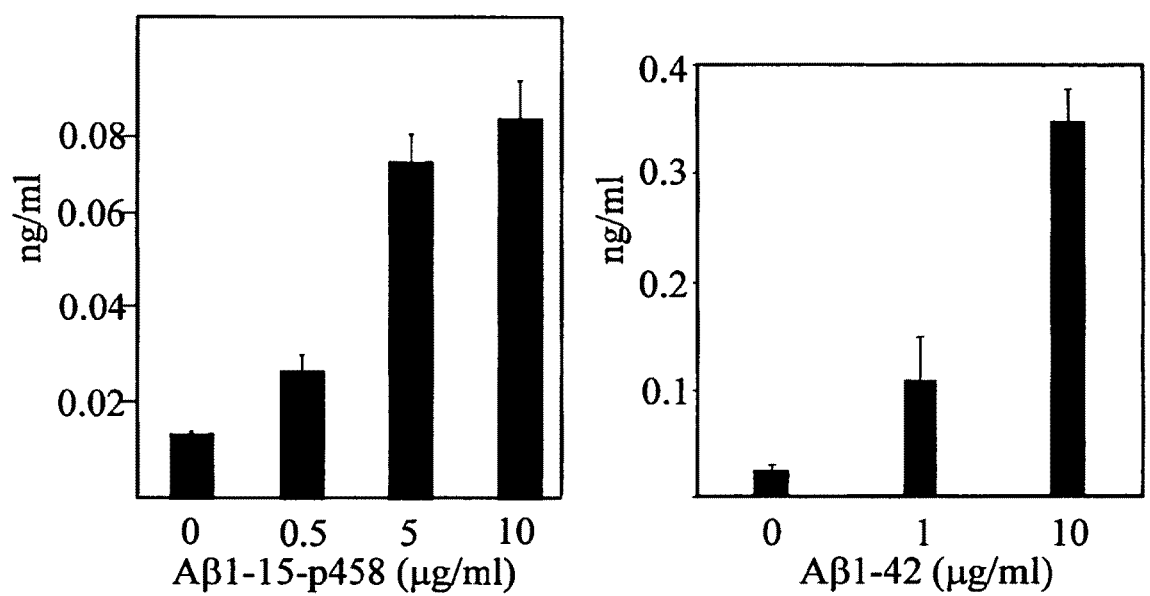
FIG. 9C, interleukin-2 secretion.

FIG. 9C shows that the HSP-activated T cells from Aβ1-42 vaccinated mice produced substantial amounts of interleukin-2 (growth factor of Th1 cells), whereas those from Aβ1-15-p458 vaccinated mice produced negligible amounts.

These data demonstrate that only a minimal T-cell activation with a Th2 phenotype is induced following Aβ1-15-p458 vaccination, in contrast to Aβ31-42 vaccination, the latter of which induces a strong Th1 proinflammatory response.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

We claim:

1. A vaccine composition for the treatment and substantial reduction of the severity or progression of a neurological disorder associated with Aβ plaque accumulation, the vaccine composition comprising a covalent conjugate consisting of an Aβ1-15 (SEQ ID NO: 9) peptide and an HSP60 peptide selected from the group consisting of p458h (SEQ ID NO: 1) and p458 (SEQ ID NO: 2); and a pharmaceutically acceptable carrier, excipient or diluent.

2. The vaccine composition according to claim 1, wherein the covalent conjugate consists of SEQ ID NO: 13 or SEQ ID NO: 17.

3. A method for treating or substantially reducing the severity or progression of a neurological disorder associated with Aβ plaque accumulation, the method comprising the step of: administering to a subject in need thereof a therapeutically effective amount of the composition according to claim 1, thereby treating or substantially reducing the severity or progression of the neurological disorder.

4. The method according to claim 3, wherein the composition is substantially free of adjuvant.

5. The method according to claim 3, wherein the neurological disorder is selected from the group consisting of Alzheimer's disease and Down's syndrome.

6. The method according to claim 3, wherein the neurological disorder is associated with a mutation in a gene encoding a protein selected from the group consisting of amyloid precursor protein (APP) and presenilin.

7. The method according to claim 3, wherein the administering comprises administering the composition at regular intervals over a period of one month to two years.

* * * * *

SEQUENCE LISTING

<160> NUMBER OF SEQ ID NOS: 17

<210> SEQ ID NO 1
<211> LENGTH: 17
<212> TYPE: PRT
<213> ORGANISM: Artificial Sequence
<220> FEATURE:
<223> OTHER INFORMATION: p458h

<400> SEQUENCE: 1

Asn Glu Asp Gln Lys Ile Gly Ile Glu Ile Ile Lys Arg Thr Leu Lys
1               5                   10                  15

Ile

<210> SEQ ID NO 2
<211> LENGTH: 17
<212> TYPE: PRT
<213> ORGANISM: Artificial Sequence
<220> FEATURE:
<223> OTHER INFORMATION: p458

<400> SEQUENCE: 2

Asn Glu Asp Gln Lys Ile Gly Ile Glu Ile Ile Lys Arg Ala Leu Lys
1               5                   10                  15

Ile

<210> SEQ ID NO 3
<211> LENGTH: 17
<212> TYPE: PRT
<213> ORGANISM: Artificial Sequence
<220> FEATURE:
<223> OTHER INFORMATION: p458mt

<400> SEQUENCE: 3

Glu Gly Asp Glu Ala Thr Gly Ala Asn Ile Val Lys Val Ala Leu Glu
1               5                   10                  15

Ala

<210> SEQ ID NO 4
<211> LENGTH: 17
<212> TYPE: PRT
<213> ORGANISM: Artificial Sequence
<220> FEATURE:
<223> OTHER INFORMATION: p458e

<400> SEQUENCE: 4

Asn Glu Asp Gln Asn Val Gly Ile Lys Val Ala Leu Arg Ala Met Glu
1               5                   10                  15

Ala

<210> SEQ ID NO 5
<211> LENGTH: 20
<212> TYPE: PRT
<213> ORGANISM: Artificial Sequence
<220> FEATURE:
<223> OTHER INFORMATION: Ec27

<400> SEQUENCE: 5

Lys Lys Ala Arg Val Glu Asp Ala Leu His Ala Thr Arg Ala Ala Val
1               5                   10                  15

Glu Glu Gly Val
            20

```
<210> SEQ ID NO 6
<211> LENGTH: 20
<212> TYPE: PRT
<213> ORGANISM: Artificial Sequence
<220> FEATURE:
<223> OTHER INFORMATION: Ec27h

<400> SEQUENCE: 6

Lys Lys Asp Arg Val Thr Asp Ala Leu Asn Ala Thr Arg Ala Ala Val
1               5                   10                  15

Glu Glu Gly Ile
            20

<210> SEQ ID NO 7
<211> LENGTH: 41
<212> TYPE: PRT
<213> ORGANISM: Artificial Sequence
<220> FEATURE:
<223> OTHER INFORMATION: AB1-42

<400> SEQUENCE: 7

Asp Ala Glu Phe Arg His Asp Ser Gly Tyr Glu Val His His Gln Lys
1               5                   10                  15

Leu Phe Phe Ala Glu Asp Val Gly Ser Asn Lys Gly Ala Ile Ile Gly
            20                  25                  30

Leu Met Val Gly Gly Val Val Ile Ala
        35                  40

<210> SEQ ID NO 8
<211> LENGTH: 40
<212> TYPE: PRT
<213> ORGANISM: Artificial Sequence
<220> FEATURE:
<223> OTHER INFORMATION: AB1-40

<400> SEQUENCE: 8

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 9
<211> LENGTH: 15
<212> TYPE: PRT
<213> ORGANISM: Artificial Sequence
<220> FEATURE:
<223> OTHER INFORMATION: AB1-15

<400> SEQUENCE: 9

Asp Ala Glu Phe Arg His Asp Ser Gly Tyr Glu Val His His Gln
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: AB1-11

<400> SEQUENCE: 10

Asp Ala Glu Phe Arg His Asp Ser Gly Tyr Glu
1               5                   10
```

<210> SEQ ID NO 11
<211> LENGTH: 12
<212> TYPE: PRT
<213> ORGANISM: Artificial Sequence
<220> FEATURE:
<223> OTHER INFORMATION: AB1-12

<400> SEQUENCE: 11

Asp Ala Glu Phe Arg His Asp Ser Gly Tyr Glu Val
1               5                   10

<210> SEQ ID NO 12
<211> LENGTH: 60
<212> TYPE: PRT
<213> ORGANISM: Artificial Sequence
<220> FEATURE:
<223> OTHER INFORMATION: SYNTHETIC PEPTDIE

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Leu Asn Glu Asp Gln Lys
            35                  40                  45

Ile Gly Ile Glu Ile Ile Lys Arg Ala Leu Lys Ile
        50                  55                  60

<210> SEQ ID NO 13
<211> LENGTH: 32
<212> TYPE: PRT
<213> ORGANISM: Artificial Sequence
<220> FEATURE:
<223> OTHER INFORMATION: SYNTHETIC PEPTIDE

<400> SEQUENCE: 13

Asp Ala Glu Phe Arg His Asp Ser Gly Tyr Glu Val His His Gln Asn
1               5                   10                  15

Glu Asp Gln Lys Ile Gly Ile Glu Ile Ile Lys Arg Ala Leu Lys Ile
                20                  25                  30

<210> SEQ ID NO 14
<211> LENGTH: 547
<212> TYPE: PRT
<213> ORGANISM: Artificial Sequence
<220> FEATURE:
<223> OTHER INFORMATION: GroEL

<400> SEQUENCE: 14

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
                20                  25                  30

Pro Lys Gly Arg Asn Val Val Leu Asp Lys Ser Phe Gly Ala Pro Thr
            35                  40                  45

Ile Thr Lys Asp Gly Val Ser Val Ala Arg Glu Ile Glu Leu Glu Asp
        50                  55                  60

Lys Phe Glu Asn Met Gly Ala Gln Met Val Lys Glu Val Ala Ser Lys
65              70                  75                  80

Ala Asn Asp Ala Ala Gly Asp Gly Thr Thr Thr Ala Thr Val Leu Ala
                85                  90                  95

-continued

```
Gln Ala Ile Ile Thr Glu Gly Leu Lys Ala Val Ala Ala Gly Met Asn
                100                 105                 110

Pro Met Asp Leu Lys Arg Gly Ile Asp Lys Ala Val Thr Ala Ala Val
            115                 120                 125

Glu Glu Leu Lys Ala Leu Ser Val Pro Cys Ser Asp Ser Lys Ala Ile
        130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
```

```
                515                 520                 525
Ala Ala Asp Leu Gly Ala Ala Gly Gly Met Gly Gly Met Gly Gly Met
    530                 535                 540

Gly Gly Met
545

<210> SEQ ID NO 15
<211> LENGTH: 573
<212> TYPE: PRT
<213> ORGANISM: Artificial Sequence
<220> FEATURE:
<223> OTHER INFORMATION: HUMAN HSP60

<400> SEQUENCE: 15

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
```

```
            325                 330                 335
Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
            355                 360                 365

Lys Arg Ile Gln Glu Ile Ile Glu Gln Leu Asp Val Thr Thr Ser Glu
            370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
                420                 425                 430

Glu Glu Gly Ile Val Leu Gly Gly Gly Cys Ala Leu Leu Arg Cys Ile
                435                 440                 445

Pro Ala Leu Asp Ser Leu Thr Pro Ala Asn Glu Asp Gln Lys Ile Gly
                450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
                515                 520                 525

Leu Leu Asp Ala Ala Gly Val Ala Ser Leu Leu Thr Thr Ala Glu Val
                530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565                 570

<210> SEQ ID NO 16
<211> LENGTH: 573
<212> TYPE: PRT
<213> ORGANISM: Artificial Sequence
<220> FEATURE:
<223> OTHER INFORMATION: MOUSE HSP60

<400> SEQUENCE: 16

Met Leu Arg Leu Pro Thr Val Leu Arg Gln Met Arg Pro Val Ser Arg
1               5                   10                  15

Ala Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
```

-continued

```
            115                 120                 125
Glu Lys Ile Ser Lys Gly Ala Asn Pro Val Glu Ile Arg Arg Gly Val
130                 135                 140
Met Leu Ala Val Asp Ala Val Ile Ala Glu Leu Lys Lys Gln Ser Lys
145                 150                 155                 160
Pro Val Thr Thr Pro Glu Glu Ile Ala Gln Val Ala Thr Ile Ser Ala
                    165                 170                 175
Asn Gly Asp Lys Asp Ile Gly Asn Ile Ile Ser Asp Ala Met Lys Lys
                180                 185                 190
Val Gly Arg Lys Gly Val Ile Thr Val Lys Asp Gly Lys Thr Leu Asn
            195                 200                 205
Asp Glu Leu Glu Ile Ile Glu Gly Met Lys Phe Asp Arg Gly Tyr Ile
210                 215                 220
Ser Pro Tyr Phe Ile Asn Thr Ser Lys Gly Gln Lys Cys Glu Phe Gln
225                 230                 235                 240
Asp Ala Tyr Val Leu Leu Ser Glu Lys Lys Ile Ser Ser Val Gln Ser
                245                 250                 255
Ile Val Pro Ala Leu Glu Ile Ala Asn Ala His Arg Lys Pro Leu Val
                260                 265                 270
Ile Ile Ala Glu Asp Val Asp Gly Glu Ala Leu Ser Thr Leu Val Leu
            275                 280                 285
Asn Arg Leu Lys Val Gly Leu Gln Val Val Ala Val Lys Ala Pro Gly
290                 295                 300
Phe Gly Asp Asn Arg Lys Asn Gln Leu Lys Asp Met Ala Ile Ala Thr
305                 310                 315                 320
Gly Gly Ala Val Phe Gly Glu Glu Gly Leu Asn Leu Asn Leu Glu Asp
                325                 330                 335
Val Gln Ala His Asp Leu Gly Lys Val Gly Glu Val Ile Val Thr Lys
                340                 345                 350
Asp Asp Ala Met Leu Leu Lys Gly Lys Gly Asp Glu Ala His Ile Glu
            355                 360                 365
Lys Arg Ile Gln Glu Ile Thr Glu Gln Leu Asp Ile Thr Thr Ser Glu
370                 375                 380
Tyr Glu Lys Glu Lys Leu Asn Glu Arg Leu Ala Lys Leu Ser Asp Gly
385                 390                 395                 400
Val Ala Val Leu Lys Val Gly Thr Ser Asp Val Glu Val Asn Glu
                405                 410                 415
Lys Lys Asp Arg Val Thr Asp Ala Leu Asn Ala Thr Arg Ala Ala Val
                420                 425                 430
Glu Glu Gly Ile Val Leu Gly Gly Gly Cys Ala Leu Leu Arg Cys Ile
            435                 440                 445
Pro Ala Leu Asp Ser Leu Lys Pro Ala Asn Glu Asp Gln Lys Ile Gly
450                 455                 460
Ile Glu Ile Ile Lys Arg Ala Leu Lys Ile Pro Ala Met Thr Ile Ala
465                 470                 475                 480
Lys Asn Ala Gly Val Glu Gly Ser Leu Ile Val Glu Lys Ile Leu Gln
                485                 490                 495
Ser Ser Ser Glu Val Gly Tyr Asp Ala Met Leu Gly Asp Phe Val Asn
                500                 505                 510
Met Val Glu Lys Gly Ile Ile Asp Pro Thr Lys Val Val Arg Thr Ala
            515                 520                 525
Leu Leu Asp Ala Ala Gly Val Ala Ser Leu Leu Thr Thr Ala Glu Ala
530                 535                 540
```

```
Val Val Thr Glu Ile Pro Lys Glu Lys Asp Pro Gly Met Gly Ala
545                 550                 555                 560

Met Gly Gly Met Gly Gly Gly Met Gly Gly Gly Met Phe
                565                 570

<210> SEQ ID NO 17
<211> LENGTH: 32
<212> TYPE: PRT
<213> ORGANISM: Artificial Sequence
<220> FEATURE:
<223> OTHER INFORMATION: SYNTHETIC PEPTIDE

<400> SEQUENCE: 17

Asp Ala Glu Phe Arg His Asp Ser Gly Tyr Glu Val His His Gln Asn
1               5                   10                  15

Glu Asp Gln Lys Ile Gly Ile Glu Ile Ile Lys Arg Thr Leu Lys Ile
            20                  25                  30
```